(12) United States Patent
Yamazaki et al.

(10) Patent No.: US 9,808,603 B2
(45) Date of Patent: Nov. 7, 2017

(54) MEDICAL INSTRUMENT

(71) Applicant: Terumo Kabushiki Kaisha, Tokyo (JP)

(72) Inventors: Ryosuke Yamazaki, Fujinomiya (JP); Satoru Suehara, Kaisei-machi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 141 days.

(21) Appl. No.: 14/667,514

(22) Filed: Mar. 24, 2015

(65) Prior Publication Data
US 2015/0196738 A1 Jul. 16, 2015

Related U.S. Application Data

(63) Continuation of application No. PCT/JP2013/074947, filed on Sep. 13, 2013.

(30) Foreign Application Priority Data

Sep. 25, 2012 (JP) .................. 2012-211513

(51) Int. Cl.
*A61M 1/00* (2006.01)
*A61B 1/00* (2006.01)
*A61M 25/06* (2006.01)
*A61M 25/01* (2006.01)
*A61M 3/02* (2006.01)
(Continued)

(52) U.S. Cl.
CPC ..... *A61M 25/0662* (2013.01); *A61B 1/00082* (2013.01); *A61B 1/0125* (2013.01);
(Continued)

(58) Field of Classification Search
CPC .......... A61M 25/0662; A61M 25/0119; A61M 25/1018; A61M 3/0279;
(Continued)

(56) References Cited

U.S. PATENT DOCUMENTS 4,582,067 A * 4/1986 Silverstein ............. A61B 1/015
600/455
RE32,158 E * 5/1986 Vukovic ................ A61B 1/015
600/123
(Continued)

FOREIGN PATENT DOCUMENTS

JP 08-047539 A 2/1996
JP 03-687110 B2 6/2005
(Continued)

OTHER PUBLICATIONS

International Search Report dated Nov. 19, 2013 issued in Application No. PCT/JP2013/074947.

*Primary Examiner* — Timothy J Neal
(74) *Attorney, Agent, or Firm* — Foley & Lardner, LLP

(57) ABSTRACT

A medical instrument includes a first elongated member including: a fluid lumen through which a fluid is flowable, an aperture opening located in a distal end surface of the first elongated member; a second elongated member including: an insertion lumen in which the first elongated member is insertable, and a discharge section through which the fluid can be discharged; and a movement section configured to form a seal between the first elongated member and the second elongated member in a state where the first elongated member is disposed in the insertion lumen of the second elongated member, the movement section being configured to allow the first elongated member and the second elongated member to move relative to each other such that the discharge section of the second elongated member is positionable on a distal side of the aperture of the first elongated member.

20 Claims, 29 Drawing Sheets

(51) Int. Cl.
*A61B 1/012* (2006.01)
*A61B 1/04* (2006.01)
*A61M 25/10* (2013.01)
*A61B 1/233* (2006.01)

(52) U.S. Cl.
CPC ............... *A61B 1/04* (2013.01); *A61B 1/233* (2013.01); *A61M 3/0279* (2013.01); *A61M 25/0119* (2013.01); *A61M 25/1018* (2013.01); *A61M 2025/0681* (2013.01); *A61M 2210/0618* (2013.01)

(58) Field of Classification Search
CPC .. A61M 2025/0681; A61M 2210/0618; A61B 1/04; A61B 1/00082; A61B 1/0125
See application file for complete search history.

(56) References Cited

U.S. PATENT DOCUMENTS

| | | | | |
|---|---|---|---|---|
| 5,823,940 A * | 10/1998 | Newman | ............ | A61B 1/00091 600/105 |
| 6,346,074 B1 * | 2/2002 | Roth | ................ | A61B 17/00234 600/121 |
| 8,012,083 B2 * | 9/2011 | Kucklick | .......... | A61M 25/0662 600/114 |
| 8,118,731 B2 * | 2/2012 | Kucklick | .......... | A61B 1/00135 600/114 |
| 8,123,676 B2 * | 2/2012 | Kucklick | .......... | A61B 1/00135 600/114 |
| 2006/0004254 A1 * | 1/2006 | Voloshin | ............ | A61B 1/00147 600/115 |
| 2006/0074274 A1 * | 4/2006 | Friedman | ........... | A61B 1/00082 600/114 |
| 2012/0143123 A1 | 6/2012 | Agnew | | |
| 2013/0053643 A1 * | 2/2013 | Yoshida | ............ | A61B 1/00006 600/114 |

FOREIGN PATENT DOCUMENTS

| | | |
|---|---|---|
| JP | T-2009-500051 A | 1/2009 |
| JP | 2011-529725 A | 12/2011 |
| WO | WO-2006/135853 A2 | 12/2006 |
| WO | WO-2010/014449 A1 | 2/2010 |

* cited by examiner

MEDICAL INSTRUMENT

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2013/074947 filed on Sep. 13, 2013, which is based upon and claims the benefit of priority of Japanese Application No. 2012-211513 filed on Sep. 25, 2012, the entire contents of which are hereby incorporated by reference in their entireties.

BACKGROUND

Technical Field

The present disclosure relates to a medical instrument to be used for supplying a fluid into a living body.

Background Art

The paranasal sinus, as a living body organ, is an intraosseous cavity adjacent to the nasal cavity, and communicates with the nasal cavity through an aperture called the natural ostium. Normally, secretion, bacteria and the like in the paranasal sinus are discharged through the natural ostium to the nasal cavity. When swelling of mucous membrane in the nasal cavity is generated by common cold-induced rhinitis, allergic rhinitis or the like or when the nasal cavity is narrowed due to septum deviation, hypertrophic rhinitis or the like, however, the natural ostium is stenosed, leading to chronic inflammation inside the paranasal sinus. Such a disease is called sinusitis.

As a treatment of sinusitis, conventionally, there has commonly been practiced a surgical treatment in which the stenosed part of the natural ostium is removed by use of forceps, a drill or the like. In recent years, on the other hand, attention has been paid to a minimally invasive treatment in which the narrowed natural ostium is dilated by a balloon catheter. For example, JP-T-2009-500051 discloses a dilating method in which a balloon catheter is operated under endoscopic observation to positionally match the balloon to the natural ostium, and the stenosed part is dilated thereby. In this method use is made of a catheter device that is provided with a predetermined lumen and that makes it possible to supply a variety of fluids to the inside of the nose and to suck out mucus, body fluid and the like present inside the nose. Since such liquids as mucus and body fluid are present in comparatively large amounts in the inside of the nose, for example, in the nasal cavity, these liquids may hamper the procedure. In addition, the liquid such as pus present in the paranasal sinus needs to be removed to the outside of the living body after the dilation of the stenosed part. By use of the aforementioned catheter device, therefore, the treatment of sinusitis can be carried out efficiently. In the case of supplying a fluid by use of the conventional catheter device, the fluid supplied into the lumen is discharged through an aperture provided at the distal end of the lumen.

In the treatment of sinusitis, it may be desired to introduce a catheter device up to the depth of the paranasal sinus for the purpose of cleaning the inside of the paranasal sinus. When a distal portion of the catheter device is formed to be longer, for instance, the distal portion of a catheter can be guided farther into a living body. The elongation of the distal portion, however, worsens the operability of the catheter main body, possibly making it bothersome to introduce the catheter into the living body. Another method may be contemplated in which a fluid tube is separately inserted in a lumen of a catheter device, and the tube is led out from the distal end of the catheter device. In this method, however, the insertion of the tube in the lumen makes it impossible to introduce other medical instruments. Consequently, an operation of replacing the tube with a treatment instrument is needed at the time of using the treatment instrument, which makes the procedure bothersome.

SUMMARY OF INVENTION

According to certain embodiments of the present invention, a medical instrument enables a fluid to be discharged in a state where a discharge section through which to discharge the fluid is positioned in an appropriate position in a living body, and enables an easy supply of the fluid to each desired part in the living body.

According to one embodiment, a medical instrument includes: a first elongated member being rigid and having a fluid lumen through which a fluid can flow and an aperture opening in a distal end surface of the first elongated member; a second elongated member being flexible and having an insertion lumen in which the first elongated member can be inserted and a discharge section through which the fluid can be discharged; and a movement section which seals between the first elongated member and the second elongated member in a state where the first elongated member is disposed in the insertion lumen of the second elongated member and which can cause the first elongated member and the second elongated member to move relative to each other so that the discharge section of the second elongated member will be positioned on a distal side of the aperture of the first elongated member.

By moving the first elongated member and the second elongated member relative to each other by the movement section, the discharge section of the second elongated member can be positioned on the distal side of the aperture of the first elongated member. Therefore, the fluid can be discharged in a state where the discharge section is positioned in an appropriate position in a living body, and the fluid can be easily supplied to each desired part in the living body.

Preferably, the medical instrument as discussed above has a configuration wherein: the discharge section of the second elongated member includes a hole through which the fluid flowing through the insertion lumen of the second elongated member can be discharged; the distal end surface of the first elongated member is connected to a distal end surface of the second elongated member; and the second elongated member is disposed in a state of being folded back toward a proximal end of the second elongated member so that the discharge section can be moved to the distal side and a proximal side of the aperture of the first elongated member.

In this configuration, the distal end surface of the first elongated member is connected to the distal end surface of the second elongated member, and the second elongated member is disposed in the state of being folded back toward the proximal end of the second elongated member. This ensures that at the time of moving the second elongated member distally relative to the first elongated member, a distalmost portion of the second elongated member that is folded back shows an enhanced rigidity, so that the opening state at the distalmost portion can be maintained easily.

In one aspect, the movement section has a seal member formed from an elastic material, the seal member being disposed between an outer surface of the first elongated member and an inner surface of the second elongated member.

In this case, since the movement section has the seal member formed from an elastic material, sealing between the first elongated member and the second elongated member is achieved easily.

In one aspect, the movement section includes an attachment part to which the second elongated member and the first elongated member are attached and a folded-back part formed by folding back the second elongated member from the attachment part toward a distal end of the second elongated member.

When this configuration is adopted, the moving amount can be limited by the length of the folded-back part. Therefore, the operator can grasp a maximum value of the moving amount, which ensures an enhanced operability of the medical instrument. In addition, collision of the second elongated member against a living body due to an excessive movement thereof can be prevented, so that a fluid can be supplied into a living body without injuring the living body.

In one aspect, the movement section has a freely expandable and contractible bellows-like expansion-and-contraction part formed at least at a part of the second elongated member.

According to this configuration, the moving amount can be limited by the length and the extent of expansion and/or contraction of the expansion-and-contraction part. Therefore, again, the operator can grasp a maximum value of the moving amount, which ensures an enhanced operability of the medical instrument. Collision of the second elongated member against a living body due to an excessive movement thereof can be obviated, so that a fluid can be supplied into a living body without injuring the living body.

In one aspect, the medical instrument further includes a moving amount adjustment section which regulates a movement of the first elongated member and the second elongated member to thereby limit a moving amount of the movement.

When this configuration is adopted, the moving amount of the movement of the first elongated member and the second elongated member can be limited by the moving amount adjustment section. This permits the operator to grasp a maximum value of the moving amount, whereby the operability of the medical instrument is enhanced. Collision of the medical instrument against a living body due to an excessive movement can be prevented, so that a fluid can be supplied into a living body without injuring the living body.

In one aspect, the second elongated member is so disposed as to be able to advance and recede along an outer surface of the first elongated member.

This configuration ensures that after a stenosed part is dilated by a balloon catheter, the second elongated member can be disposed in the dilated stenosed part by only moving the second elongated member distally. Consequently, a fluid can be easily supplied into the living body.

In one aspect, the medical instrument has a configuration wherein: the first elongated member has a first taper section where a diameter of the fluid lumen gradually increases from a distal side toward a proximal side; the second elongated member has a second taper section where a diameter of the insertion lumen gradually increases from the distal side toward the proximal side; and the first taper section and the second taper section are disposed in an axially positionally matched state in a condition where the first elongated member is disposed in the insertion lumen but the first elongated member and the second elongated member have not yet been moved relative to each other.

In this configuration, the medical instrument has a tapered-off shape on the distal side, which ensures an enhanced insertability of the medical instrument into a living body.

In one aspect, the first elongated member has a bend section formed on a distal side.

With the first elongated member thus provided with the bend section on the distal side, the insertability of the medical instrument into a living body that is complicated in shape is enhanced. In addition, when the second elongated member is moved distally relative to the first elongated member, the second elongated member is also formed on the distal side with a bend section along the bend section of the first elongated member. Consequently, a fluid can be easily supplied into a living body that is complicated in shape.

In one aspect, the medical instrument further includes: a fluid supply section permitting a fluid to be supplied therethrough into a gap formed between the first elongated member and the second elongated member; and a fluid suction section permitting a fluid to be sucked out through the fluid lumen of the first elongated member.

This configuration makes it possible not only to supply a fluid into a living body but also to suck out mucus and/or body fluid present in the living body, whereby the function of the medical instrument is enhanced.

In one aspect, the medical instrument as discussed above is used as a medical instrument for cleaning a living body organ present inside a nose of a living body.

In this case, a living body organ present inside a nose of a living body can be cleaned by use of the medical instrument. Accordingly, the medical instrument can be used as a medical instrument for treatment of sinusitis.

DETAILED DESCRIPTION

First Embodiment

Figure 1:
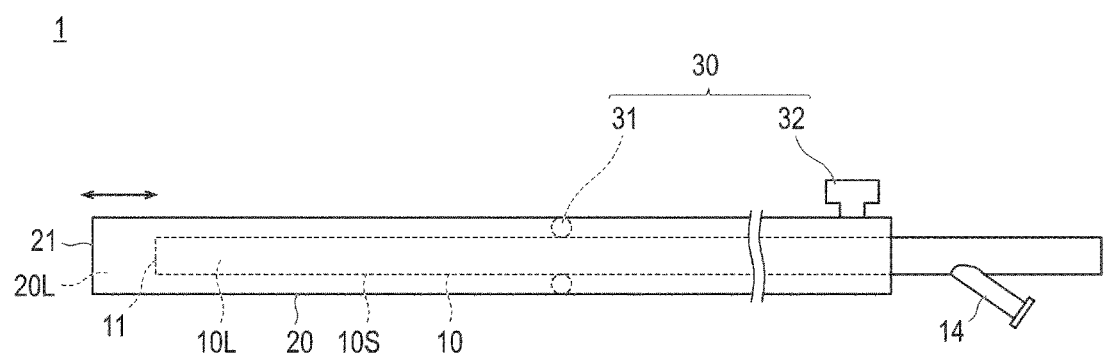
FIG. 1 is a schematic view of a medical instrument according to a first embodiment of the present disclosure.

Embodiments, disclosed by way of example, of the present disclosure will be described below, referring to the drawings. Note that, for convenience of explanation, dimensional ratios in the drawings may be exaggerated and be different from the actual ratios. In the following description, the hand operation side of a medical instrument 1 according to a first embodiment of the present disclosure will be referred to as "proximal side," and the side of insertion of the medical instrument 1 into a living body lumen as "distal side."

The configuration of the medical instrument 1 according to the first embodiment of the present disclosure will be described.

Figure 2:
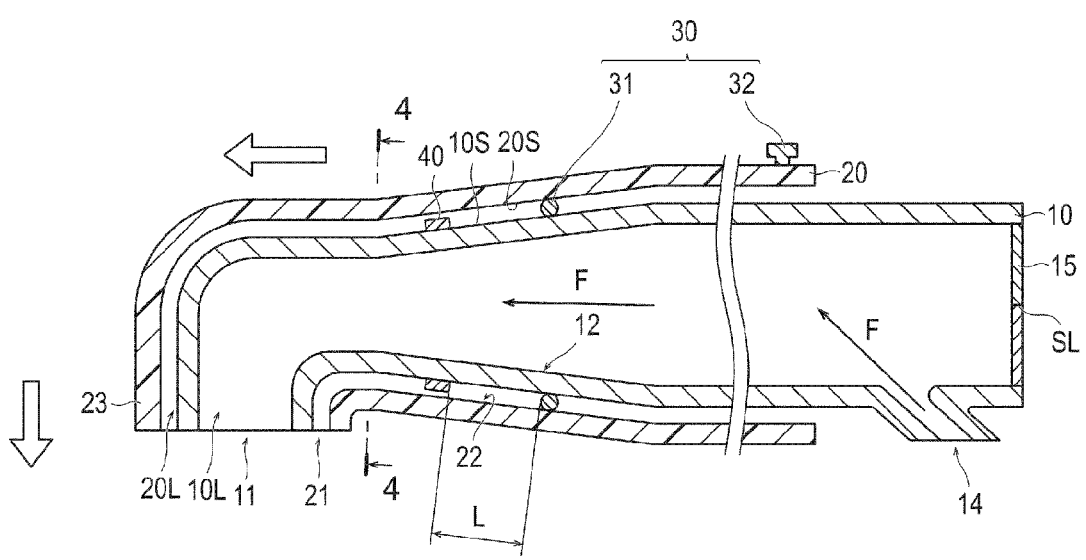
FIG. 2 is a front sectional view of the medical instrument according to the first embodiment of the present disclosure.
Figure 3:
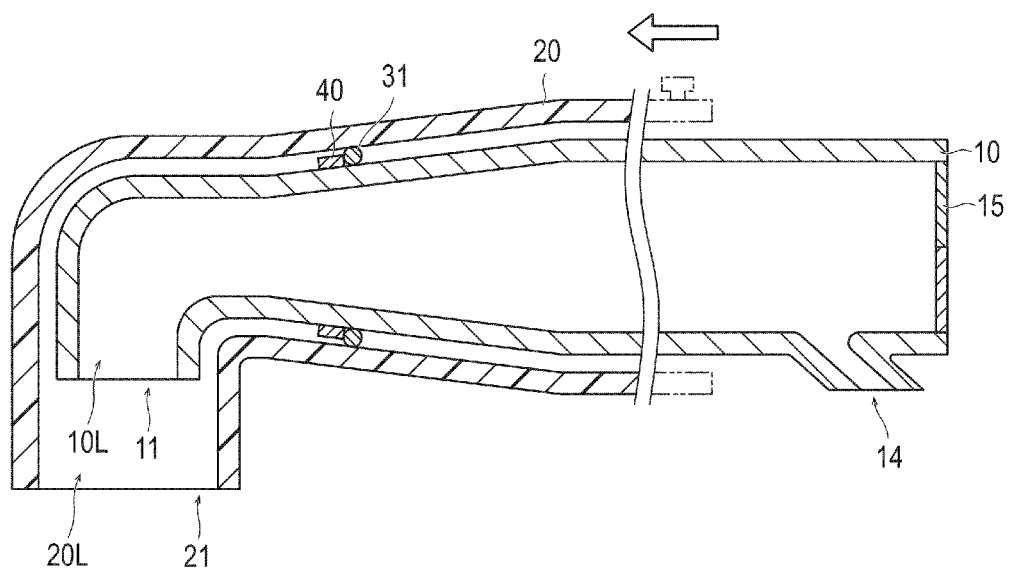
FIG. 3 is a front sectional view showing a state where a discharge section of a second elongated member is positioned on a distal side of an aperture of a first elongated member.
Figure 4:
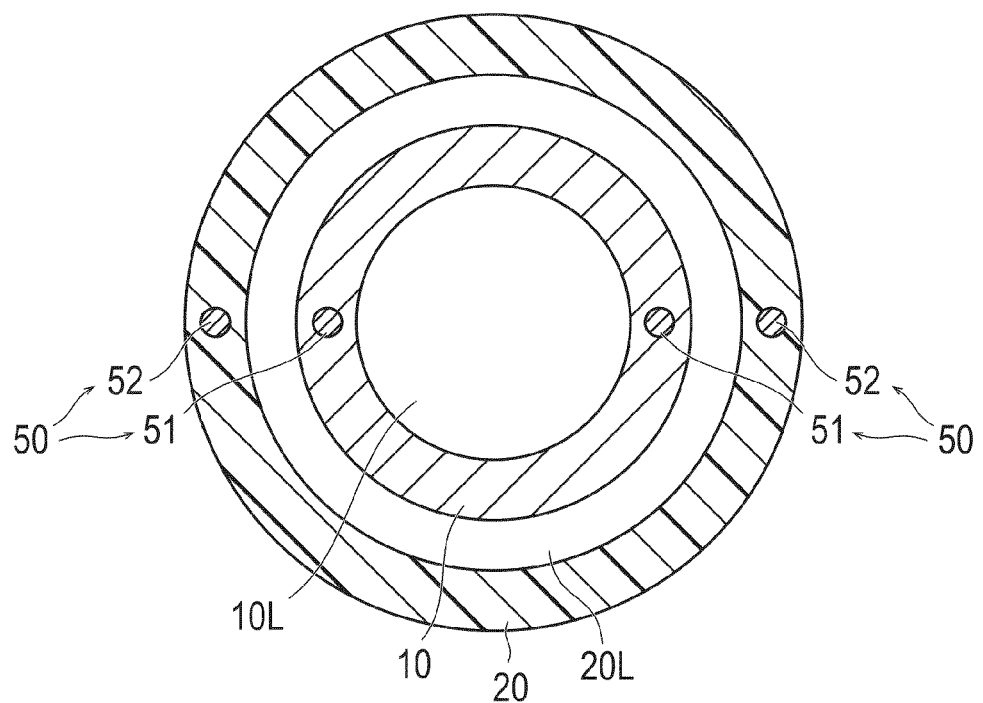
FIG. 4 is a sectional view taken alone line 4-4 of FIG. 2.

FIG. 1 is a schematic view showing the medical instrument 1 according to the first embodiment of the present disclosure. FIG. 2 is a front sectional view showing the medical instrument 1 according to the first embodiment of the disclosure. FIG. 3 is a front sectional view showing a state where a discharge section 21 of a second elongated member 20 is positioned on a distal side in relation to an aperture 11 of a first elongated member 10. FIG. 4 is a sectional view taken along line 4-4 of FIG. 2.

The medical instrument 1 according to the first embodiment of the present disclosure will be outlined as follows. As shown in FIG. 1, the medical instrument 1 includes: the first elongated member 10 being rigid and having a fluid lumen 10L through which a fluid F can flow and the aperture 11 opening in a distal end surface of the first elongated member 10; the second elongated member 20 being flexible and having an insertion lumen 20L in which the first elongated member 10 can be inserted and the discharge section 21 through which the fluid F can be discharged; and a movement section 30 which seals between the first elongated member 10 and the second elongated member 20 in a state where the first elongated member 10 is disposed in the insertion lumen 20L of the second elongated member 20 and which can cause the second elongated member 20 to advance and recede along an outer surface 10S of the first elongated member 10 so that the discharge section 21 of the second elongated member 20 will be positioned on the distal side in relation to the aperture 11 of the first elongated member 10. The medical instrument 1 will be described in detail below.

As shown in FIGS. 2 to 4, the medical instrument 1 includes: the first elongated member 10 being rigid and having the fluid lumen 10L through which the fluid F can flow and the aperture 11 opening in the distal end surface of the first elongated member 10; the second elongated member 20 being flexible and having the insertion lumen 20L in which the first elongated member 10 can be inserted and the discharge section 21 through which the fluid F can be discharged; the movement section 30 which seals between the first elongated member 10 and the second elongated member 20 in a state where the first elongated member 10 is disposed in the insertion lumen 20L of the second elongated member 20 and which can cause the second elongated member 20 to advance and recede along the outer surface 10S of the first elongated member 10 so that the discharge section 21 of the second elongated member 20 will be positioned on the distal side in relation to the aperture 11 of the first elongated member 10; a moving amount adjustment section 40 which regulates a movement of the second elongated member 20 so as to limit a moving amount L of the second elongated member 20; and rigidity members 50 provided in the inside of the first elongated member 10 and of the second elongated member 20.

The first elongated member 10 forms therein the fluid lumen 10L through which the fluid F can flow. The fluid F is supplied into a living body organ through the aperture 11 provided in the distal end surface of the first elongated member 10. The first elongated member 10 includes: the aperture 11 opening in the distal end surface thereof; a first taper section 12 where the diameter of the fluid lumen 10L gradually increases from the distal side toward the proximal side; a bend section 13 formed on the distal side; and a supply section 14 which is formed on the proximal side and through which the fluid F is supplied into the fluid lumen 10L. In addition, a seal section 15 for preventing the fluid F from flowing out via the proximal side is fixed to the proximal side of the fluid lumen 10L. The material constituting the first elongated member 10 is a metallic material such as stainless steel. The material, however, is not limited to the metallic material such as stainless steel, and other metallic materials and highly rigid resin materials can also be used.

The aperture 11 is provided in the distal end surface of the first elongated member 10, and the fluid F is supplied therethrough from the first lumen 10L into the insertion lumen 20L.

The first taper section 12 is so formed that the diameter of the fluid lumen 10L gradually increases from the distal side toward the proximal side.

The bend section 13 is provided for the purpose of enhancing insertability of the medical instrument 1 into a living body which is complicated in shape. The angle at which the bend section 13 is bent is, for example, 90 degrees, but this is not limiting, and the angle may be 30, 60 or 110 degrees, for example.

The supply section 14 serves for supplying the fluid F therethrough from a fluid reservoir (not shown) into the fluid lumen 10L. The fluid reservoir and the supply section 14 are interconnected in a liquid-tight or gas-tight manner by a known tube.

The seal section 15 is so configured that the fluid F is prevented from flowing out via the proximal end of the fluid lumen 10L and a balloon catheter 100 (described later) can be inserted thereinto. The seal section 15 may be, for example, a seal member (valve body) formed therein with a slit SL, but this is not restrictive.

The fluid F is supplied into a living body, for the purpose of, for example, washing the inside of the living body. The fluid F may be, for example, physiological saline solution, but this is not limiting.

The second elongated member 20 forms therein the insertion lumen 20L in which the first elongated member 10 can be inserted and which enables the second elongated member 20 to advance and recede along the outer surface 10S of the first elongated member 10. The second elongated member 20 includes: the discharge section 21 through which the fluid F can be discharged; a second taper section 22 where the diameter of the insertion lumen 20L gradually increases from the distal side toward the proximal side; and a bend section 23 formed on the distal end. The material constituting the second elongated member 20 may be, for example, a highly biocompatible thermoplastic resin such as fluoro-resins such as ETFE (tetrafluoroethylene-ethylene copolymer), PTFE (polytetrafluoroethylene), etc., polyolefins such as PE (polyethylene), PP (polypropylene), etc., polyamides, polyesters, polyurethane, and so on.

The discharge section 21 is configured as an aperture shape provided at the distal end surface of the second elongated member 20, and the discharge section 21 permits the fluid F to be discharged therethrough into a living body.

The second taper section 22 is so configured that the diameter of the insertion lumen 20L gradually increases from the distal side toward the proximal side.

The bend section 23 assumes a shape along the bent shape of the bend section 13 of the first elongated member 10 because the second elongated member 20 is flexible. Thus, the bend section 23 of the second elongated member 20 has a shape similar to that of the bend section 13 of the first elongated member 10.

The first taper section 12 and the second taper section 22 are disposed in an axially positionally matched state in a state where the first elongated member 10 is disposed inside the insertion lumen 20L but the second elongated member 20 has not yet been moved relative to the first elongated member 10.

The movement section 30 seals between the first elongated member 10 and the second elongated member 20, and the movement section 30 permits the second elongated member 20 to advance and recede along the outer surface 10S of the first elongated member 10. The movement section 30 includes: a seal member 31 formed from an elastic material and disposed between the outer surface 10S of the first elongated member 10 and an inner surface 20S of the second elongated member 20; and an operating part 32 fixed to a proximal-end outer periphery of the second elongated member 20 and operated to move the second elongated member 20 distally.

The seal member 31 seals between the first elongated member 10 and the second elongated member 20. The seal member 31 is fixed to the inner surface 20S of the second elongated member 20, but is not fixed to the outer surface 10S of the first elongated member 10. This configuration ensures that when the second elongated member 20 is moved distally by operating the operating part 32, the seal member 31 is moved distally together with the distal movement of the second elongated member 20, and abuts on the moving amount adjustment section 40 upon moving a predetermined distance, so that the moving amount L of the second elongated member 20 can be limited. The seal member 31 may be, for example, an O-ring-like seal member. The outside diameter of the seal member 31 is set to be smaller than the width defined by the outer surface 10S of the first elongated member 10 and the inner surface 20S of the second elongated member 20. Note that the method of fixing the seal member 31 and the inner surface 20S of the second elongated member 20 to each other is not specifically restricted. For example, the fixation may be carried out by use of an adhesive or the like.

The operating part 32 is operated, for example by pushing it distally with a finger, to cause the second elongated member 20 fixed to the operating part 32 to move distally. The method of fixing the operating part 32 and the second elongated member 20 to each other is not particularly limited. For example, the fixation may be performed by use of an adhesive or the like.

The moving amount adjustment section 40 regulates the movement of the first elongated member 10 and the second elongated member 20, thereby limiting the moving amount L. The moving amount adjustment section 40 is fixed to the outer surface 10S of the first elongated member 10, on the distal side in relation to the seal member 31. The moving amount L is equal to the distance by which the seal member 31 and the moving amount adjustment section 40 are spaced apart in the state before the second elongated member 20 is moved relative to the first elongated member 10. The method of fixing the moving amount adjustment section 40 and the outer surface 10S of the first elongated member 10 is not specifically restricted. For example, the fixation may be carried out by use of an adhesive, soldering, brazing, welding or the like. Note that a structure similar to the moving amount adjustment section 40 may be disposed on the proximal side in relation to the seal member 31, for the purpose of adjusting a proximal moving amount.

The rigidity members 50 enhance the rigidity of the medical instrument 1 in a direction orthogonal to the bending direction of the bend section 13 of the first elongated member 10 and the bend section 23 of the second elongated member 20. As shown in FIG. 4, the rigidity members 50 include first rigidity members 51 provided in the inside of the first elongated member 10 and second rigidity members 52 provided in the inside of the second elongated member 20. The first rigidity members 51 are provided on both left and right sides with respect to a direction (the horizontal direction in FIG. 3) orthogonal to the bending direction (the downward direction in FIG. 3) of the bend sections 13 and 23. Also, the second rigidity members 52 are provided on both left and right sides with respect to the direction orthogonal to the bending direction. The rigidity members 50 may be, but are not restricted to, wires, for example. With the above-mentioned configuration, the rigidity members 50 can set a low rigidity in the bending direction, while enhancing the overall rigidity of the medical instrument 1 as compared with the case where the medical instrument 1 is not provided with the rigidity members 50.

Now, referring to FIGS. 5 to 9, a method of supplying the fluid F into a living body having a stenosed part by use of the medical instrument 1 according to the first embodiment of the present disclosure will be described below.

In the following description, a paranasal sinus will be taken as an example of a living body organ to be supplied with the fluid F, and there will be shown an example of application of the medical instrument 1 according to the first embodiment to a living body with a stenosed part formed at a natural ostium K providing communication between the paranasal sinus and a nasal cavity. Briefly, after dilation of the stenosed part formed at the natural ostium K, the fluid F is supplied into the paranasal sinus (frontal sinus, sphenoidal sinus, maxillary sinus) present on the tip of the natural ostium K. Note that while the paranasal sinus and the nasal cavity are omitted in FIGS. 5 to 9, the nasal cavity exists on a side of the natural ostium K on which the medical instrument 1 is present, and the paranasal sinus exists on the opposite side. In FIGS. 5 to 9, for easier understanding, the medical instrument 1 is illustrated in front sectional view, whereas the balloon catheter 100 is depicted in front view. The method will be described in detail below.

Figure 5:
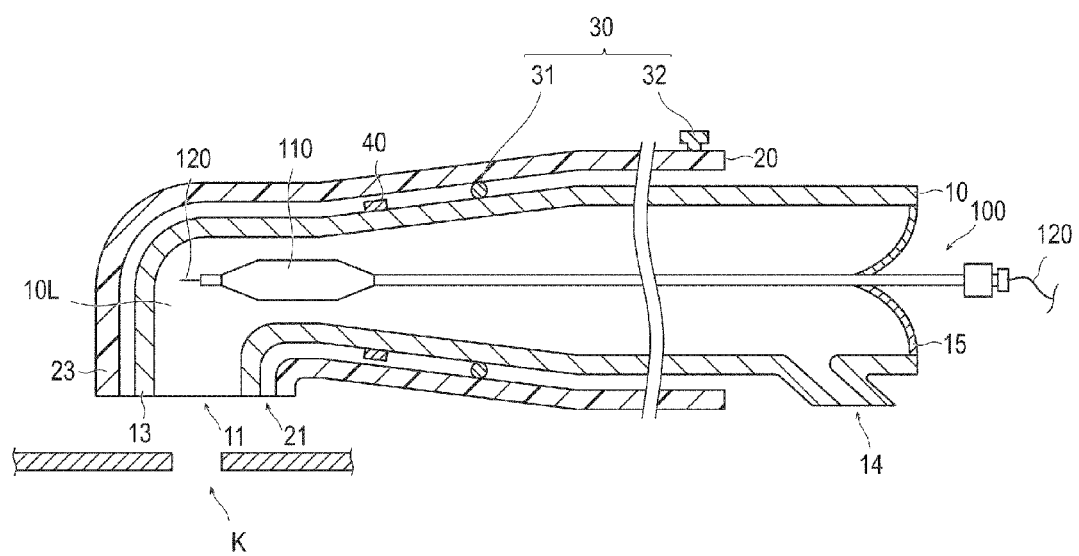
FIG. 5 is a diagram showing a state where a medical instrument with a balloon catheter inserted in a fluid lumen is inserted in a nasal cavity.

First, as shown in FIG. 5, an operator inserts the medical instrument 1, with the balloon catheter 100 inserted into the fluid lumen 10L to such an extent as not to protrude beyond the aperture 11, into the nasal cavity via an entrance to the nose. At the time of inserting the balloon catheter 100 into the medical instrument 1 via the seal section 15, a guide wire 120 is preliminarily inserted in the medical instrument 1, and the balloon catheter 100 is inserted along the guide wire 120 thus preliminarily inserted. Note that the balloon catheter 100 is an over-the-wire type balloon catheter. This, however, is not restrictive, and the balloon catheter 100 may be an RX-type balloon catheter.

Figure 6:
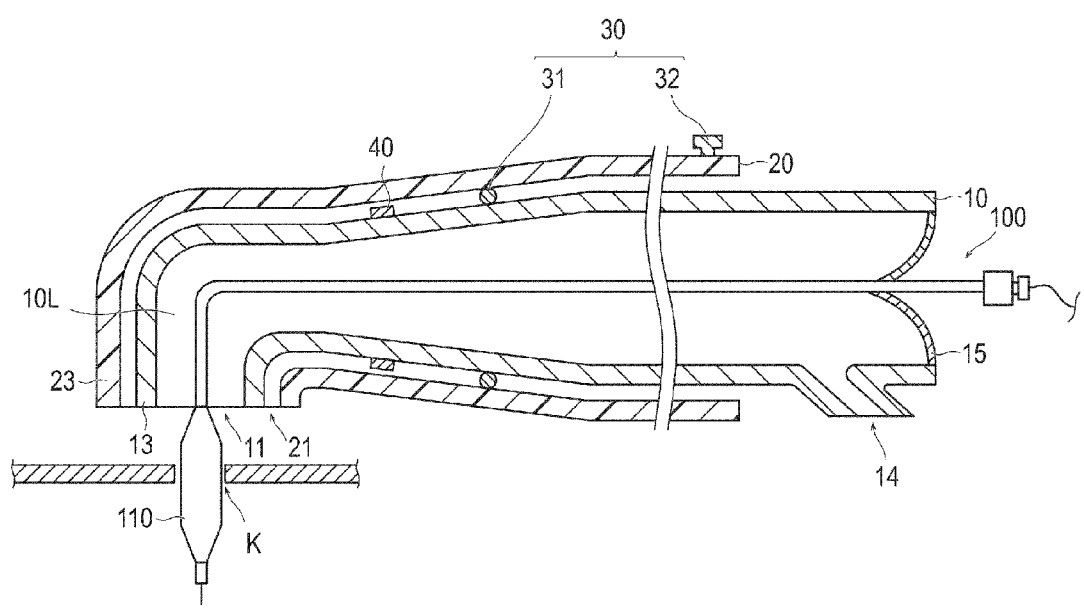
FIG. 6 is a diagram showing a state where a balloon is disposed in a stenosed natural ostium.

Next, the operator operates the guide wire 120 to pass it through the natural ostium K until it reaches the inside of the paranasal sinus. Thereafter, the operator gradually pushes the balloon catheter 100 distally along the guide wire 120, and protrudes the balloon catheter 100 from the aperture 11 of the first elongated member 10, to dispose a balloon 110 of the balloon catheter 100 in the stenosed natural ostium K, as shown in FIG. 6.

Figure 7:
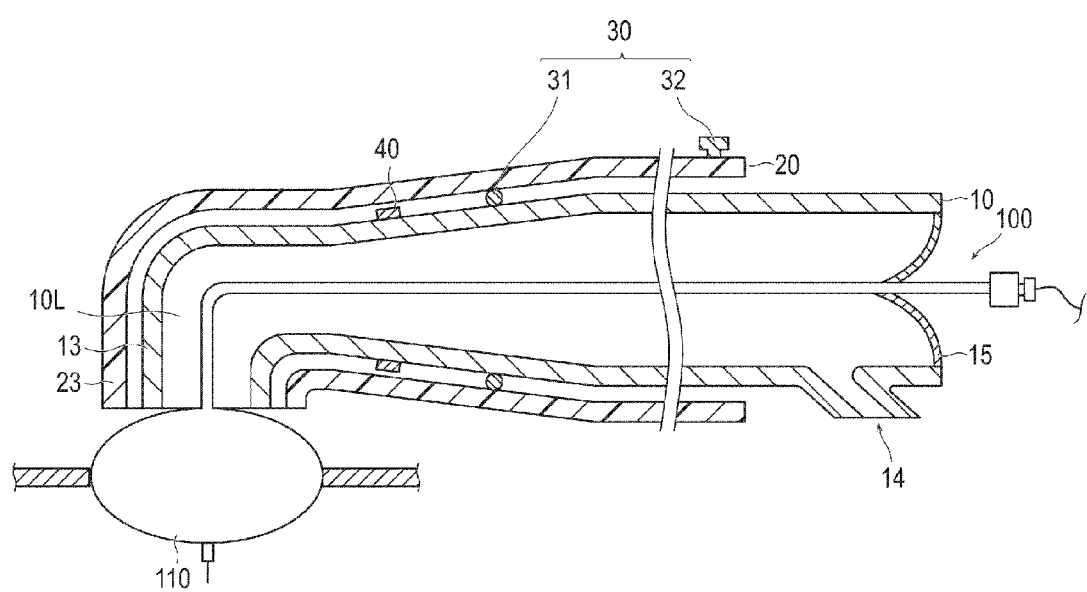
FIG. 7 is a diagram showing a state where the balloon of the balloon catheter is inflated to dilate the natural ostium.

Subsequently, as shown in FIG. 7, the operator inflates the balloon 110 of the balloon catheter 100, to dilate the stenosed natural ostium K.

Figure 8:
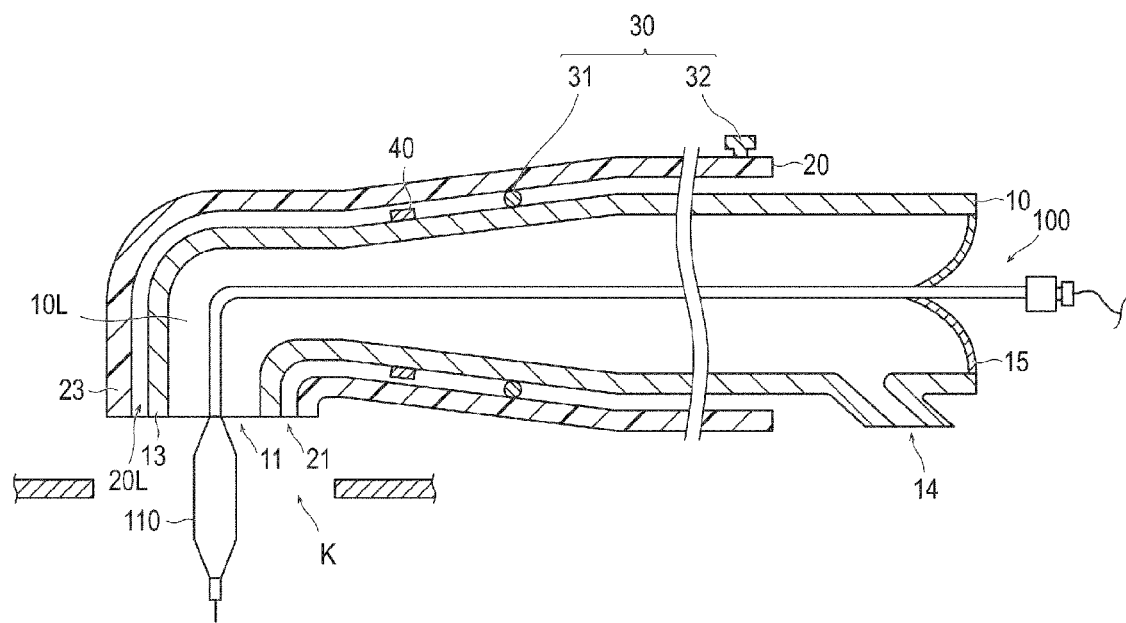
FIG. 8 is a diagram showing a state where the balloon of the balloon catheter is deflated.

Next, as shown in FIG. 8, the operator deflates the balloon 110 of the balloon catheter 100. In this instance, since the natural ostium K has been deformed by the balloon 110, it remains in the dilated state.

Figure 9:
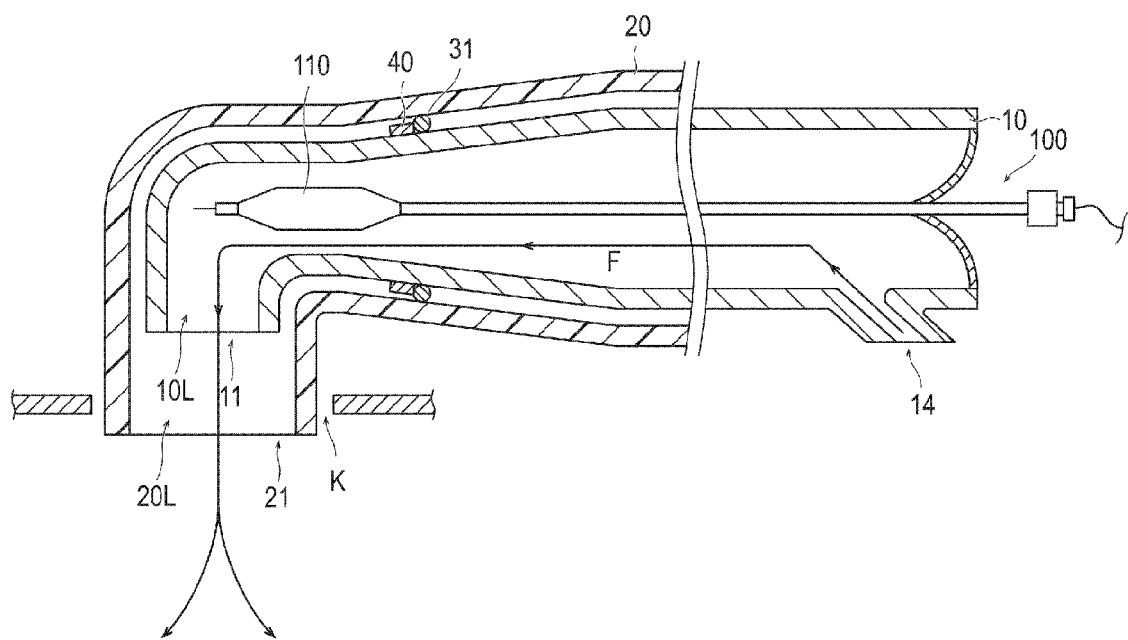
FIG. 9 is a diagram showing a manner in which the discharge section of the second elongated member is positioned on the distal side of the aperture of the first elongated member and a fluid is supplied.

Subsequently, as shown in FIG. 9, the operator pushes out the operating part 32 distally, whereby the discharge section 21 of the second elongated member 20 fixed to the operating part 32 is moved to the distal side in relation to the dilated natural ostium K. This step is followed by supplying the fluid F into the paranasal sinus. In this instance, the fluid F is prevented from flowing out via the proximal end of the fluid lumen 10L, since the seal section 15 is fixed to the proximal end of the fluid lumen 10L.

The fluid F, after being supplied from the fluid reservoir into the fluid lumen 10L through the supply section 14, moves from the proximal side toward the distal side, is supplied through the aperture 11 into the insertion lumen 20L, and is discharged via the discharge section 21 to be supplied into the paranasal sinus.

As aforementioned, the method of supplying the fluid F into a living body having a stenosed part by use of the medical instrument 1 includes: (i) a step in which the first elongated member having the fluid lumen through which a fluid can flow and the aperture opening in a distal end surface of the first elongated member is inserted into the insertion lumen formed in the flexible second elongated member having the discharge section permitting the fluid to be discharged therethrough, followed by sealing between the first elongated member and the second elongated member, and, in this state, the first elongated member and the second elongated member are introduced into the living body; (ii) a step of putting the first elongated member and the second elongated member into a relative movement in the axial direction so as to position the discharge section on the distal side in relation to the aperture; and (iii) a step of causing the fluid to move from the proximal side toward the distal side in the fluid lumen, thereby discharging the fluid via the discharge section.

In addition, the method is characterized in that in step (ii), the movement of the first elongated member and the second elongated member is regulated by the moving amount adjustment section to limit the moving amount.

The method is characterized in that in step (ii), the second elongated member is moved relative to the first elongated member.

As aforementioned, according to the first embodiment of the present disclosure, by moving the second elongated member 20 relative to the first elongated member 10 by the movement section 30 it is possible to position the discharge section 21 of the second elongated member 20 on the distal side in relation to the aperture 11 of the first elongated member 10. Therefore, the fluid can be discharged in a state where the position of the discharge section 21 is set in an appropriate position in a living body, and, consequently, the fluid F can be easily supplied into the paranasal sinus.

The movement section 30 has the seal member 31 formed from an elastic material and disposed between the outer surface 10S of the first elongated member 10 and the inner surface 20S of the second elongated member 20. Therefore, the gap between the first elongated member 10 and the second elongated member 20 can be easily sealed.

The medical instrument 1 further includes the moving amount adjustment section 40 which regulates the movement of the second elongated member 20 relative to the first elongated member 10 to thereby limit the moving amount L. Therefore, the operator can grasp a maximum value of the moving amount L, and the operability is enhanced. In addition, collision of the second elongated member 20 against the paranasal sinus due to an excessive movement thereof can be prevented, so that the fluid F can be supplied into the paranasal sinus without injuring the paranasal sinus.

The second elongated member 20 is so provided as to be able to advance and recede along the outer surface 10S of the first elongated member 10. Therefore, by simply moving the second elongated member 20 distally after the natural ostium K is dilated by the balloon catheter 100, it is possible to dispose the second elongated member 20 in the dilated natural ostium K, and thereby to easily supply the fluid F into the paranasal sinus.

The first elongated member 10 has the first taper section 12 where the diameter of the fluid lumen 10L gradually increases from the distal side toward the proximal side, and the second elongated member 20 has the second taper section 22 where the diameter of the insertion lumen 20L gradually increases from the distal side toward the proximal side. In a state where the first elongated member 10 is disposed in the insertion lumen 20L but the second elongated member 20 has not yet been moved relative to the first elongated member 10, the first taper section 12 and the second taper section 22 are disposed in an axially positionally matched state. Therefore, the medical instrument 1 is shaped to have a more reduced diameter on the distal side, which ensures enhanced insertability of the medical instrument 1 into the paranasal sinus.

The first elongated member 10 has the bend section 13 formed on the distal side. Therefore, the insertability of the medical instrument 1 into a complicated-shaped paranasal sinus is enhanced. In addition, when the second elongated member 20 is moved distally, the bend section 23 of the second elongated member 20 is also formed on the distal side along the bend section 13 of the first elongated member 10, so that the fluid F can be easily supplied into the paranasal sinus, which has a complicated shape.

The medical instrument 1 is used as a medical instrument 1 for cleaning a living body organ present in the inside of a nose of a living body. Therefore, the inside of a paranasal sinus can be cleaned, and the medical instrument 1 can be used for treatment of sinusitis.

Second Embodiment

A second embodiment of the present disclosure will now be described below. Descriptions of those features which are common to the first and second embodiments will be omitted, and features that are characteristic of only the second embodiment will be described.

Figure 10:
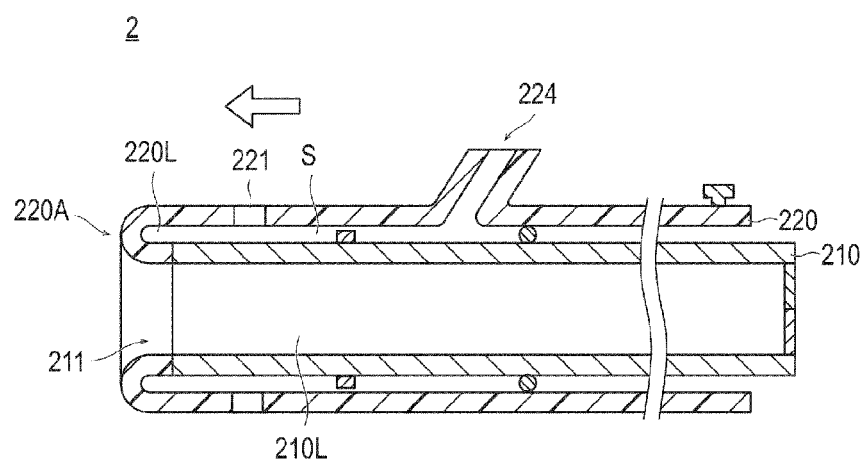
FIG. 10 is a front sectional view showing a medical instrument according to a second embodiment of the present disclosure.
Figure 11:
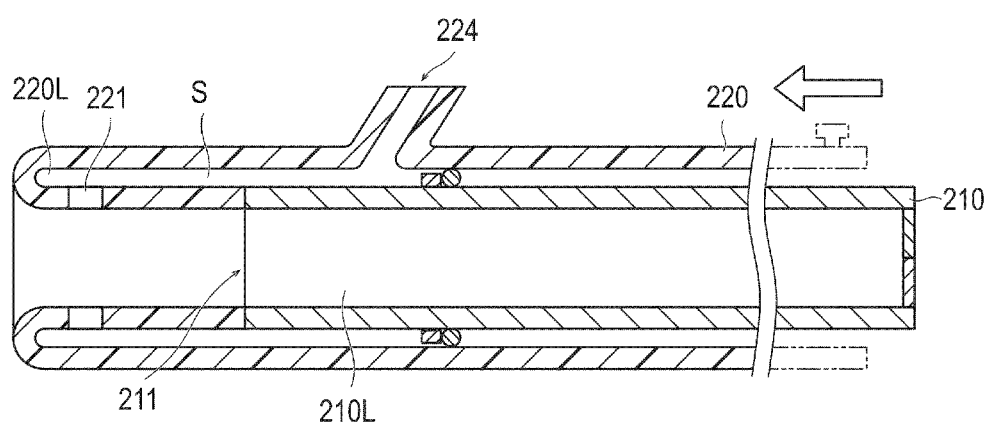
FIG. 11 is a front sectional view showing a state where a discharge section of a second elongated member is positioned on a distal side of an aperture of a first elongated member, in the second embodiment of the present disclosure.

FIG. 10 is a front sectional view showing a medical instrument 2 according to the second embodiment of the present disclosure. FIG. 11 is a front sectional view showing a state where a discharge section 221 of a second elongated member 220 is positioned on a distal side in relation to an aperture 211 of a first elongated member 210, in the second embodiment of the disclosure.

As shown in FIGS. 10 and 11, the medical instrument 2 according to the second embodiment of the present disclosure includes: the first elongated member 210 being rigid and having a fluid lumen 210L through which a fluid F can flow and the aperture 211 opening in a distal end surface of the first elongated member 210; and the second elongated member 220 being flexible and having an insertion lumen 220L in which the first elongated member 210 can be inserted and the discharge section 221 through which the fluid F can be discharged. The other points of the configuration of the medical instrument 2 are the same as those in the first embodiment.

A distal end surface of the first elongated member 210 is connected to a distal end surface of the second elongated member 220. The method of connecting these end surfaces is not specifically restricted; for example, the connection may be carried out by use of an adhesive or the like.

The second elongated member 220 has a supply section 224 through which the fluid F is to be supplied into the fluid lumen 210L by way of the insertion lumen 220L in a state where the second elongated member 220 has been moved distally.

The discharge section 221 is composed essentially of a hole through which the fluid F flowing in the insertion lumen 220L of the second elongated member 220 can be discharged. A configuration is adopted in which, with the second elongated member 220 disposed in a state of being folded back toward the proximal end of the second elongated member 220, the discharge section 221 can be moved to the distal side and the proximal side in relation to the aperture 211 of the first elongated member 210. Note that in FIG. 10 the discharge section 221 is present on the proximal side in relation to the aperture 211 of the first elongated member 210, whereas in FIG. 11 the discharge section 221 is present on the distal side in relation to the aperture 211 of the first elongated member 210. The discharge section 221, which is disposed on the side of the outer periphery of the first elongated member 210 and on an extension line on the distal side of the second elongated member 220 as shown in FIG. 10 before the second elongated member 220 is pushed out, is disposed on an extension line on the distal side of the first elongated member 210 as shown in FIG. 11, and the fluid F is supplied via the discharge section 221 into the fluid lumen 210L, after the second elongated member 220 is pushed out distally. Note that the area to which the fluid F is supplied is not restricted to the inside of the fluid lumen 210L, and the fluid F can also be supplied, for example, in the direction of the outer peripheries of the first elongated member 210 and the second elongated member 220 by adjusting the amount by which the second elongated member 220 is pushed out toward the distal side.

The supply section 224 permits the fluid F to be supplied from a fluid reservoir (not shown) into a gap S between the first elongated member 210 and the second elongated member 220, in a state where the second elongated member 220 has been moved distally.

Now, referring to FIGS. 12(A) and 12(B), a method of supplying the fluid F into a paranasal sinus by use of the medical instrument 2 according to the second embodiment of the present disclosure will be described below. Here, the description will be made only of a step of supplying the fluid F into the paranasal sinus through a natural ostium K that is in a dilated state.

Figure 12A:
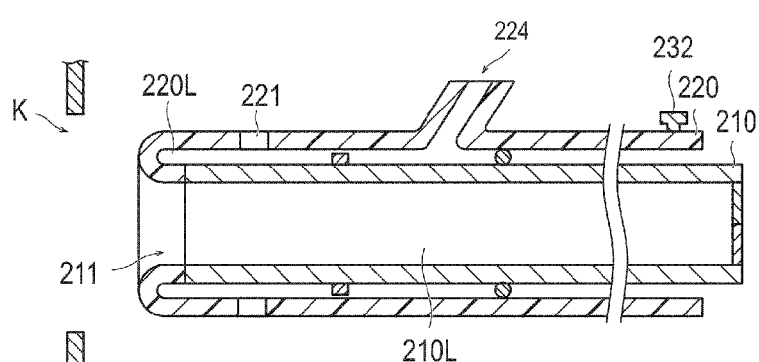
FIG. 12(A) is a front sectional view of the medical instrument according to the second embodiment of the present disclosure after a natural ostium is dilated.

FIG. 12(A) is a front sectional view of the medical instrument 2 according to the second embodiment of the present disclosure in a state after the natural ostium K is dilated. FIG. 12(B) is a front sectional view showing the medical instrument 2 according to the second embodiment in its state when the fluid F is supplied under the condition where the discharge section 221 of the second elongated member 220 is positioned on the distal side of the aperture 211 of the first elongated member 210.

Figure 12B:
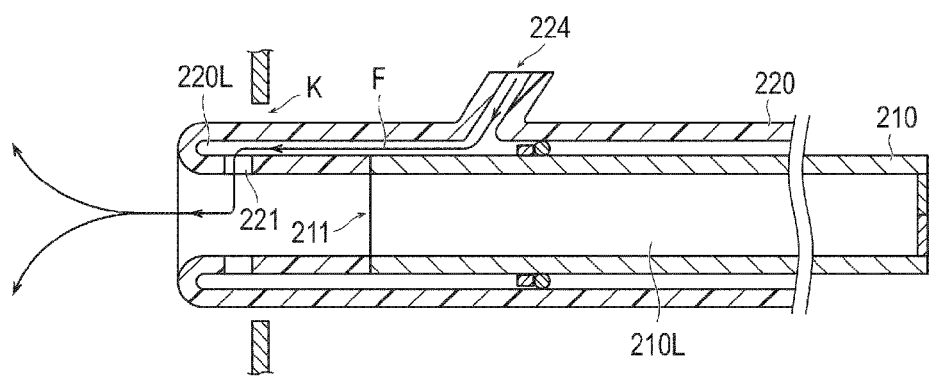
FIG. 12(B) is a front sectional view showing the medical instrument according to the second embodiment when the discharge section of the second elongated member is positioned on the distal side of the aperture of the first elongated member and a fluid is supplied.

As shown in FIGS. 12(A) and 12(B), after dilating the natural ostium K, the operator pushes out an operating part 232 distally so that the discharge section 221 of the second elongated member 220 fixed to the operating part 232 is thereby moved to the distal side of the dilated natural ostium K, whereby the fluid F is supplied into the paranasal sinus.

After being supplied from the fluid reservoir into the gap S formed between the first elongated member 210 and the second elongated member 220 by way of the supply section 224, the fluid F moves from the proximal side toward the distal side and is discharged through the discharge section 211 to be supplied into the paranasal sinus.

As described above, according to the second embodiment of the present disclosure, the distal end surface of the first elongated member 210 is connected to the distal end surface of the second elongated member 220, and the second elongated member 220 is disposed in the state of being folded back toward the proximal end thereof. When the second elongated member 220 is moved distally, therefore, the rigidity of the second elongated member 220 at its distalmost portion 220A which has been folded back is enhanced, and the opening state at the distalmost portion 220A can be maintained easily.

Third Embodiment

A third embodiment of the present disclosure will now be described below. Descriptions of those features which are common to the third embodiment and the first and second embodiments will be omitted, and features that are characteristic of only the third embodiment will be described.

Figure 13:
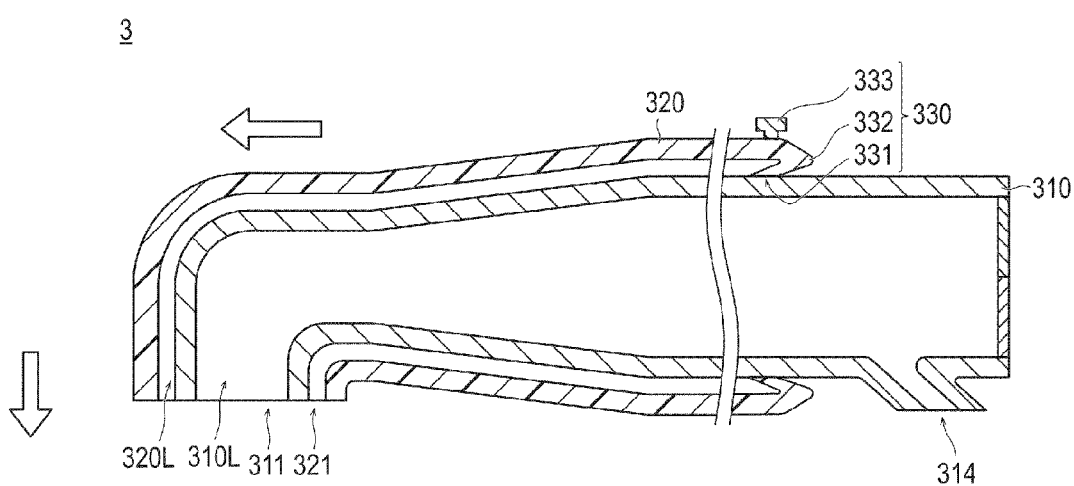
FIG. 13 is a front sectional view showing a medical instrument according to a third embodiment of the present disclosure.
Figure 14:
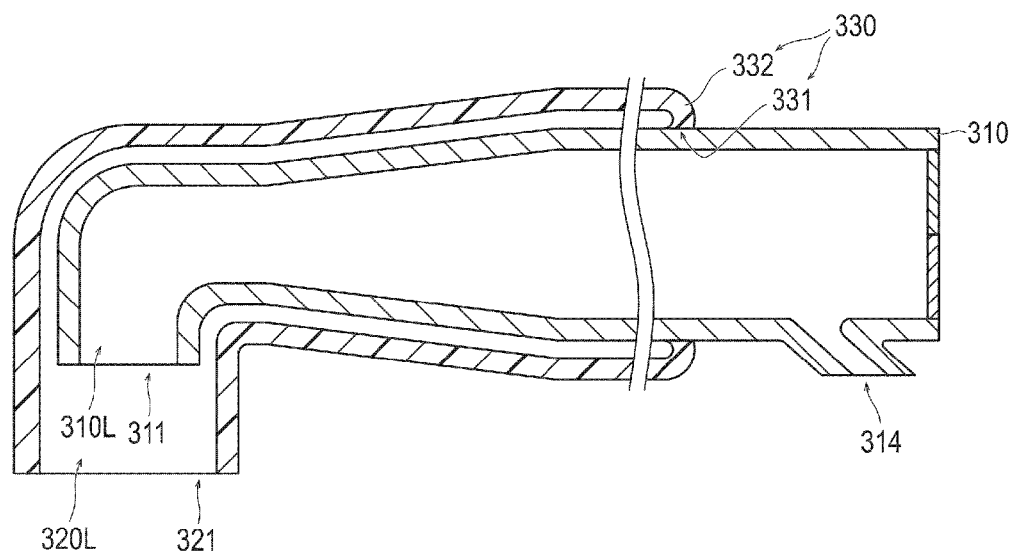
FIG. 14 is a front sectional view showing a state where a discharge section of a second elongated member is positioned on a distal side of an aperture of a first elongated member, in the third embodiment of the present disclosure.

FIG. 13 is a front sectional view showing a medical instrument 3 according to the third embodiment of the present disclosure. FIG. 14 is a front sectional view showing a state in which a discharge section 321 of a second elongated member 320 is positioned on the distal side of an aperture 311 of a first elongated member 310, in the third embodiment of the present disclosure.

As shown in FIGS. 13 and 14, the medical instrument 3 according to the third embodiment of the present disclosure includes: the first elongated member 310 being rigid and having a fluid lumen 310L through which a fluid F can flow and the aperture 311 opening in a distal end surface of the first elongated member 310; the second elongated member 320 being flexible and having an insertion lumen 320L in which the first elongated member 310 can be inserted and the discharge section 321 through which the fluid F can be discharged; a movement section 330 which seals between the first elongated member 310 and the second elongated member 320 in a state where the first elongated member 310 is disposed in the insertion lumen 320L of the second elongated member 320 and which can cause the second elongated member 320 to advance and recede along an outer surface 310S of the first elongated member 310 so that the discharge section 321 of the second elongated member 320 will be positioned on the distal side of the aperture 311 of the first elongated member 310.

The movement section 330 includes: an attachment part 331 to which the second elongated member 320 and the first elongated member 310 are attached; and a folded-back part 332 formed by folding back the second elongated member 320 from the attachment part 331 toward the distal side. The movement section 330 further has an operating part 333 which is fixed to a proximal-end outer periphery of the second elongated member 320 and which is operated to move the second elongated member 320 distally. With the movement section 330 configured as above, a moving amount L is determined by the length of the folded-back part 332, and, therefore, it is unnecessary to provide the moving amount adjustment section 40 possessed by the medical instrument 1 according to the first embodiment. Such a moving amount adjustment section, however, may be provided in order to determine the moving amount L more precisely.

Now, referring to FIGS. 15(A) and 15(B), a method of supplying the fluid F into a paranasal sinus having a stenosed natural ostium K by use of the medical instrument 3 according to the third embodiment of the present disclosure will be described below. Here, description will be made only of a step of supplying the fluid F into the paranasal sinus via the natural ostium K which is in a dilated state.

Figure 15A:
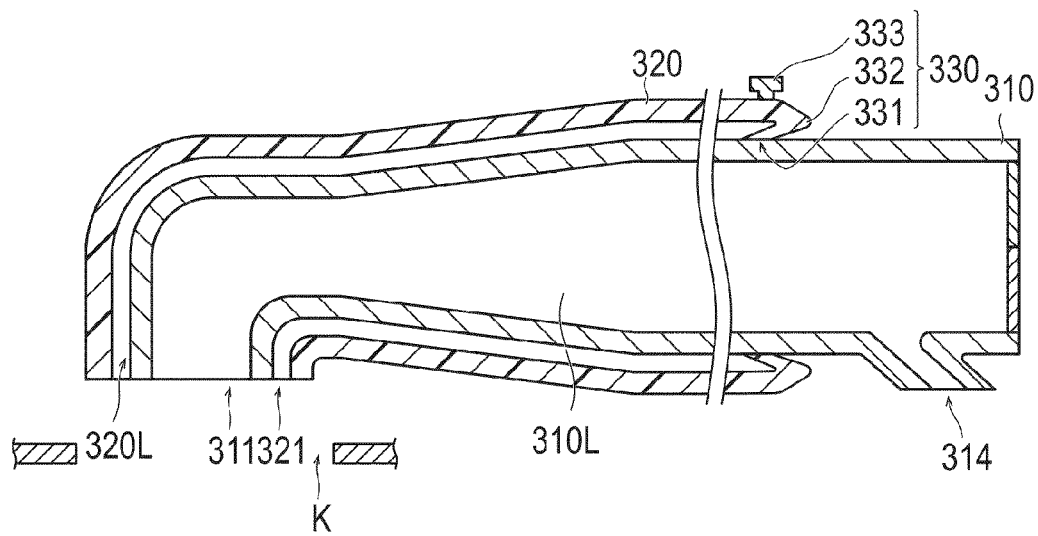
FIG. 15(A) is a front sectional view of the medical instrument according to the third embodiment of the present disclosure after a natural ostium is dilated.

FIG. 15(A) is a front sectional view of the medical instrument 3 according to the third embodiment of the present disclosure in a state after the natural ostium K is dilated. FIG. 15(B) is a front sectional view showing the medical instrument 3 according to the third embodiment in a state when the fluid F is supplied under the condition where the discharge section 321 of the second elongated member 320 is positioned on the distal side of the aperture 311 of the first elongated member 310.

Figure 15B:
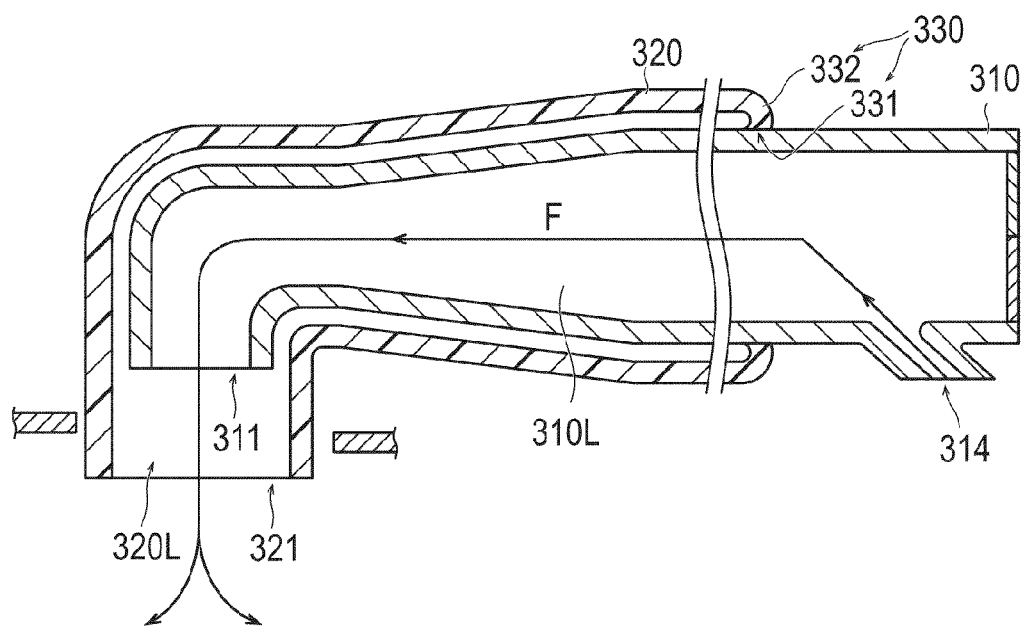
FIG. 15(B) is a front sectional view showing the medical instrument according to the third embodiment when the discharge section of the second elongated member is positioned on the distal side of the aperture of the first elongated member and a fluid is supplied.

As shown in FIGS. 15(A) and 15(B), after dilating the natural ostium K, the operator pushes out the operating part 333 distally so that the discharge section 321 of the second elongated member 320 fixed to the operating part 333 is thereby moved to the distal side of the dilated natural ostium K, whereby the fluid F is supplied into the paranasal sinus.

After being supplied from a fluid reservoir into the fluid lumen 310L through a supply section 314, the fluid F moves from the proximal side toward the distal side, is supplied through the aperture 311 into the insertion lumen 320L, and is discharged via the discharge section 321 to be supplied into the paranasal sinus.

As described above, according to the third embodiment of the present disclosure, the moving amount L can be limited by the length of the folded-back part 332. Therefore, the operator can grasp a maximum value of the moving amount L, so that the operability of the medical instrument 3 is enhanced. In addition, collision of the second elongated member 320 against the paranasal sinus due to an excessive movement thereof can be prevented, so that the fluid F can be supplied into the paranasal sinus without injuring the paranasal sinus.

Fourth Embodiment

A fourth embodiment of the present disclosure will now be described below. Descriptions of those features which are common to the fourth embodiment and the first to third embodiments will be omitted, and features that are characteristic of only the fourth embodiment will be described.

Figure 16:
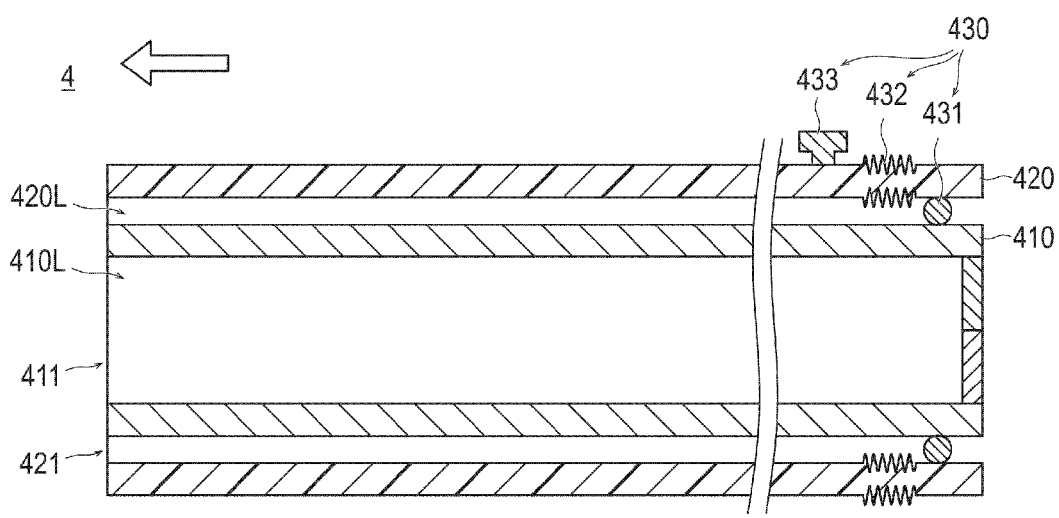
FIG. 16 is a front sectional view showing a medical instrument according to a fourth embodiment of the present disclosure.
Figure 17:
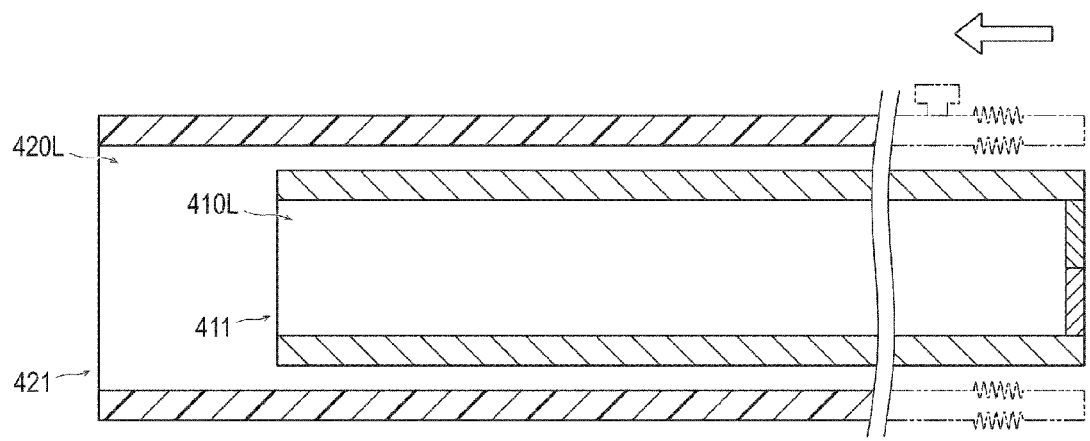
FIG. 17 is a front sectional view showing a state where a discharge section of a second elongated member is positioned on a distal side of an aperture of a first elongated member, in the fourth embodiment of the present disclosure.

FIG. 16 is a front sectional view showing a medical instrument 4 according to the fourth embodiment of the present disclosure. FIG. 17 is a front sectional view showing a state in which a discharge section 421 of a second elongated member 420 is positioned on the distal side of an aperture 411 of a first elongated member 410, in the fourth embodiment of the present disclosure.

As shown in FIGS. 16 and 17, the medical instrument 4 according to the fourth embodiment of the present disclosure includes: the first elongated member 410 being rigid and having a fluid lumen 410L through which a fluid F can flow and the aperture 411 opening in a distal end surface of the first elongated member 410; the second elongated member 420 being flexible and having an insertion lumen 420L in which the first elongated member 410 can be inserted and the discharge section 421 through which the fluid F can be discharged; a movement section 430 which seals between the first elongated member 410 and the second elongated member 420 in a state where the first elongated member 410 is disposed in the insertion lumen 420L of the second elongated member 420 and which can cause the second elongated member 420 to advance and recede along an outer surface 410S of the first elongated member 410 so that the discharge section 421 of the second elongated member 420 will be positioned on the distal side of the aperture 411 of the first elongated member 410.

The movement section 430 includes: a seal member 431 formed from an elastic material and disposed between the outer surface 410S of the first elongated member 410 and an inner surface 420S of the second elongated member 420; and an expandable and contractible bellows-like expansion-and-contraction part 432 formed at a part of the second elongated member 420. The movement section 430 further has an operating part 433 which is fixed to an outer periphery on the proximal side of the second elongated member 420 and which is operated to move the second elongated member 420 distally. With the movement section 430 configured as above, a moving amount L is determined according to the length and the extent of expansion/contraction of the expansion-and-contraction part 432, so that it is unnecessary to provide the moving amount adjustment section 40 possessed by the medical instrument 1 according to the first embodiment. Such a moving amount adjustment section, however, may be provided in order to determine the moving amount L more precisely.

The expansion-and-contraction part 432, by expanding and contracting, causes the second elongated member 420 to advance and recede. The expansion-and-contraction part 432 is disposed between the seal member 431 and the operating part 433 of the second elongated member 420.

Now, referring to FIGS. 18(A) and 18(B), a method of supplying the fluid F into a paranasal sinus having a stenosed natural ostium K by use of the medical instrument 4 according to the fourth embodiment of the present disclosure will be described below. Here, description will be made only of a step of supplying the fluid F into the paranasal sinus via the natural ostium K in a dilated state.

Figure 18A:
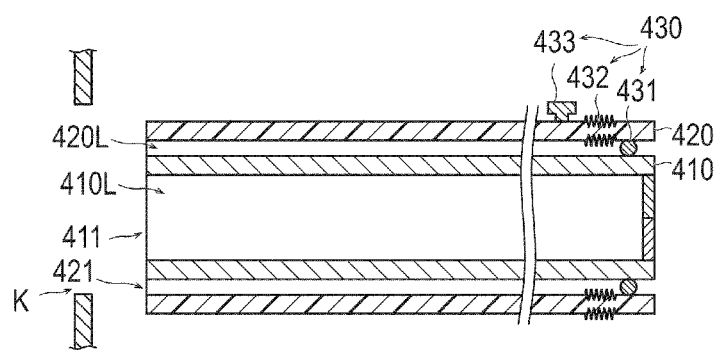
FIG. 18(A) is a front sectional view of the medical instrument according to the fourth embodiment of the present disclosure after a natural ostium is dilated.

FIG. 18(A) is a front sectional view of the medical instrument 4 according to the fourth embodiment of the present disclosure in a state after the natural ostium K is dilated. FIG. 18(B) is a front sectional view showing the medical instrument 4 according to the fourth embodiment in a state when the fluid F is supplied under the condition where the discharge section 421 of the second elongated member 420 is positioned on the distal side of the aperture 411 of the first elongated member 410.

Figure 18B:
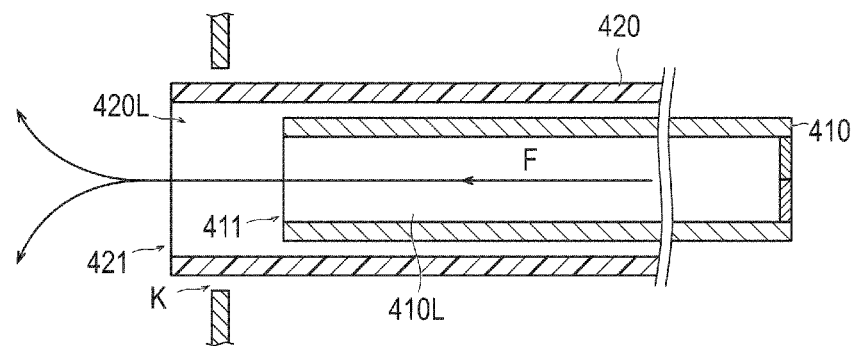
FIG. 18(B) is a front sectional view showing the medical instrument according to the fourth embodiment when the discharge section of the second elongated member is positioned on the distal side of the aperture of the first elongated member and a fluid is supplied.

As shown in FIGS. 18(A) and 18(B), after dilating the natural ostium K, the operator pushes out the operating part 433 distally so that the discharge section 421 of the second elongated member 420 fixed to the operating part 433 is thereby moved distally beyond the dilated natural ostium K, whereby the fluid F is supplied into the paranasal sinus.

After being supplied from a fluid reservoir into the fluid lumen 410L through a supply section (not shown), the fluid F moves from the proximal side toward the distal side, is supplied through the aperture 411 into the insertion lumen 420L, and is discharged via the discharge section 421 to be supplied into the paranasal sinus.

As aforementioned, according to the fourth embodiment of the present disclosure, the moving amount L can be limited according to the length and the extent of expansion/contraction of the expansion-and-contraction part 432. Therefore, the operator can grasp a maximum value of the moving amount L, so that the operability of the medical instrument 4 is enhanced. Besides, collision of the second elongated member 420 against the paranasal sinus due to an excessive movement thereof can be prevented. Consequently, the fluid F can be supplied into the paranasal sinus without injuring the paranasal sinus.

Fifth Embodiment

A fifth embodiment of the present disclosure will now be described below. Descriptions of those features which are common to the fifth embodiment and the first to fourth embodiments will be omitted, and features that are characteristic of only the fifth embodiment will be described.

Figure 19:
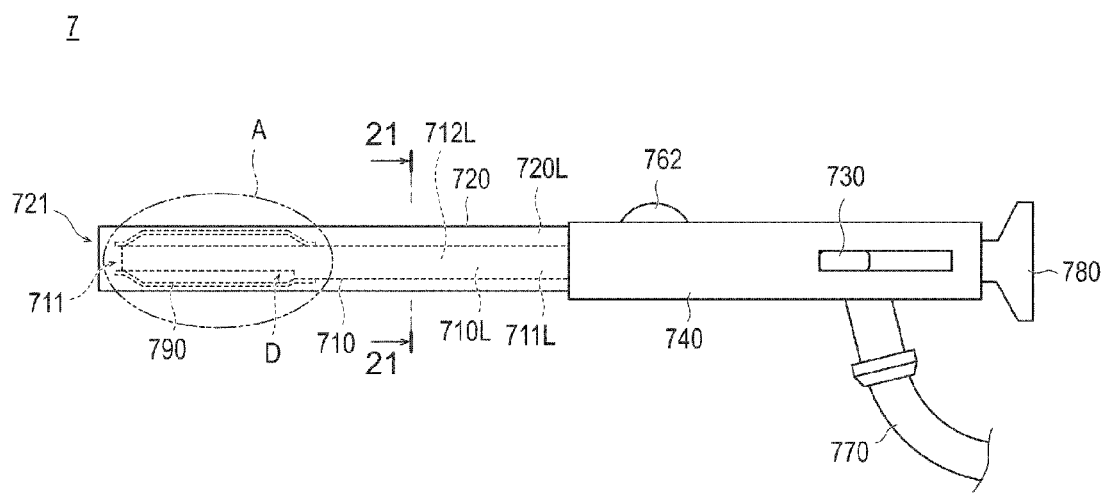
FIG. 19 is a schematic view showing a medical instrument according to a fifth embodiment of the present disclosure.
Figure 20:
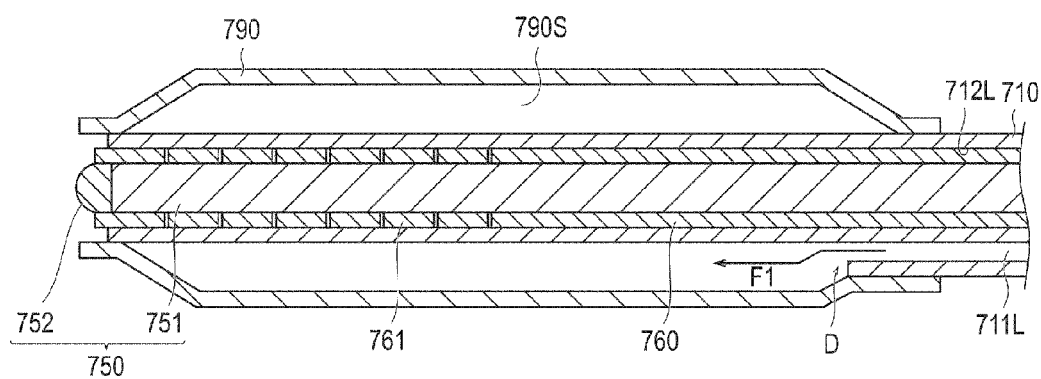
FIG. 20 is a partial enlarged sectional view showing part A of FIG. 19.
Figure 21:
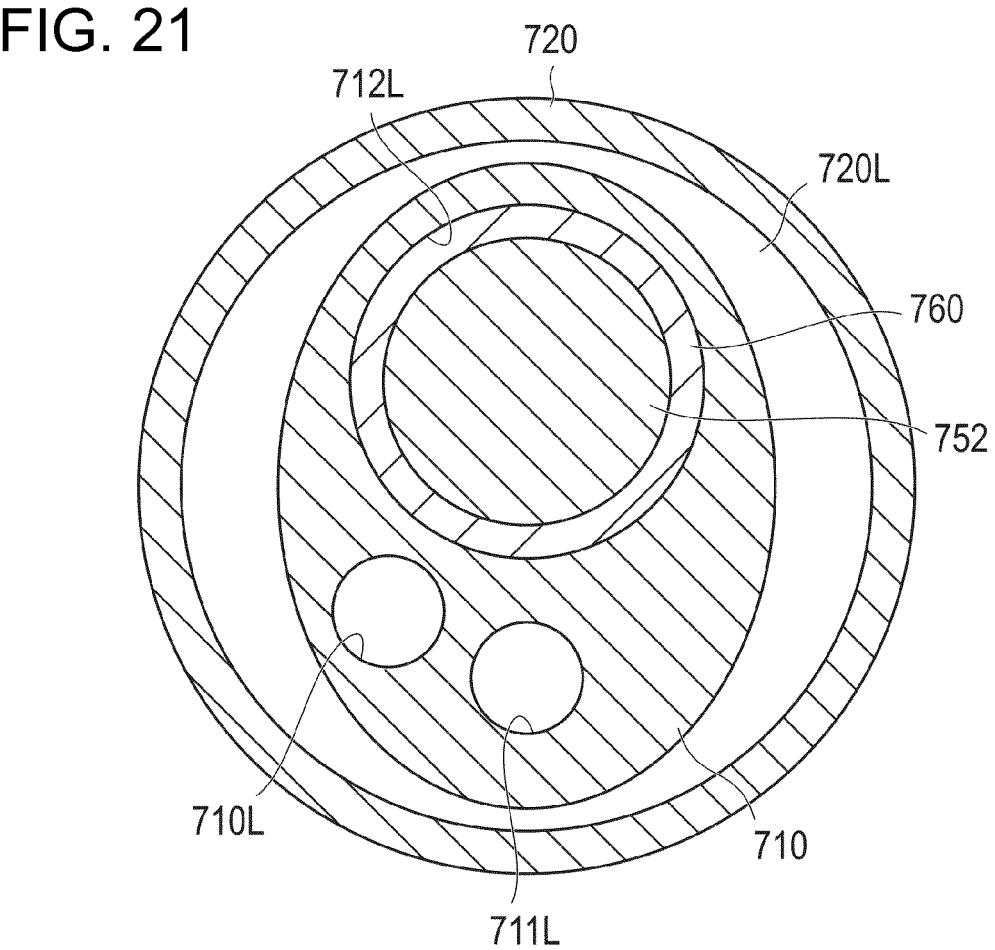
FIG. 21 is a sectional view taken along line 21-21 of FIG. 19.

FIG. 19 is a schematic view showing a medical instrument 7 according to the fifth embodiment of the present disclosure. FIG. 20 is a partial enlarged sectional view showing part A of FIG. 19. In FIG. 20, a second elongated member 720 is omitted, for a clearer illustration. FIG. 21 is a sectional view taken along line 21-21 of FIG. 19.

The medical instrument 7 according to the fifth embodiment of the present disclosure will be outlined as follows. As shown in FIGS. 19 to 21, the medical instrument 7 includes: a first elongated member 710 being rigid and having a fluid lumen 710L through which a fluid F can flow and an aperture 711 opening in a distal end surface of the first elongated member 710; and the second elongated member 720 being flexible and having an insertion lumen 720L in which the first elongated member 710 can be inserted and a discharge section 721 through which the fluid F can be discharged. The medical instrument 7 according to the fifth embodiment further includes a movement section 730 which seals between the first elongated member 710 and the second elongated member 720 in a state where the first elongated member 710 is disposed in the insertion lumen 720L of the second elongated member 720 and which can cause the second elongated member 720 to advance and recede relative to the first elongated member 710 so that the discharge section 721 of the second elongated member 720 will be positioned on the distal side of the aperture 711 of the first elongated member 710. The medical instrument 7 according to the fifth embodiment will now be described in detail below.

The medical instrument 7 includes the first elongated member 710, the second elongated member 720, the movement section 730, a main body section 740, an imaging device 750, a third elongated member 760, a supply section 770, a connection section 780, and an inflation section 790.

As shown in FIG. 21, the first elongated member 710 includes the fluid lumen 710L through which the fluid F can flow, an inflating lumen 711L through which an inflating fluid F1 for inflating the inflation section 790 can flow, an imaging device lumen 712L in and through which the imaging device 750 can be inserted and passed. At the distal side, the inflation section 790 is fixed to an outer periphery of the first elongated member 710 in an inflatable manner. The fluid lumen 710L and the imaging device lumen 712L are provided to penetrate the first elongated member 710 up to the distal end. As shown in FIGS. 19 and 20, the first elongated member 710 has a step D in a position in its extending direction, and the inflating lumen 711L is provided ranging to the step D. The inflating lumen 711L communicates with a space 790S provided inside the inflation section 790.

The second elongated member 720 has the insertion lumen 720L in which the first elongated member 710 and the inflation section 790 can be inserted, and the discharge section 721 through which the fluid F can be discharged. The second elongated member 720 is so provided as to be slidable within the main body section 740 by the movement section 730.

The movement section 730 causes the second elongated member 720 to advance and recede relative to the first elongated member 710. The movement section 730 is disposed on the proximal side of the main body section 740. With the movement section 730 slid to the right side, the inflation section 790 is exposed from the second elongated member 720. With the movement section 730 slid to the left side, on the other hand, the discharge section 721 of the second elongated member 720 is positioned on the distal side of the aperture 711 of the first elongated member 710.

The movement section 730, a bending operating part 762 which will be described later, the supply section 770, and the connection section 780 are attached to the main body section 740. In addition, though not illustrated, sealing between the first elongated member 710 and the second elongated member 720 is performed inside the main body section 740.

As shown in FIG. 20, the imaging device 750 picks up an image of an area ranging from a nasal cavity to the inside of a paranasal sinus. The imaging device 750 includes a lens 752 as well as an imaging section 751 for picking up an image.

The third elongated member 760 is disposed around the outer periphery of the imaging device 750, inside the imaging device lumen 712L. The third elongated member 760 is provided on the distal side thereof with a bend section 761 which can be bent. The bend section 761 is configured to be bendable by the bending operating part 762 attached to the main body section 740. The bending operating part 762 may be, for example, of a dial type, which when rotated bends the bend section 761. The orientation of the first elongated member 710, the imaging device 750, and the inflation section 790 can be changed as the bend section 761 is bent.

The supply section 770 permits the fluid F to be supplied therethrough into the fluid lumen 710. In addition, the supply section 770 permits the inflating fluid F1 to be supplied into the inflating lumen 711L therethrough. Furthermore, the supply section 770 permits the inflating fluid F1 present in the space 790S of the inflation section 790 to be drawn out therethrough.

The connection section 780 is connected to a monitor section of a PC (personal computer), for example, and an image picked up by the imaging device 750 is displayed on the monitor section.

The inflation section 790 is inflated by a flow of the inflating fluid F1 into the space 790S, thereby to dilate a stenosed part formed at a natural ostium K, like the balloon 110 in the first embodiment described above.

The inflating fluid F1 may be gas or liquid. Examples of the inflating fluid F1 include gases such as helium gas, CO2 gas, O2 gas, etc. and liquids such as physiological saline solution, a contrast medium, etc.

Now, referring to FIGS. 22 to 25, a method of supplying the fluid F into a paranasal sinus having a stenosed part by use of the medical instrument 7 according to the fifth embodiment will be described below.

Figure 22:
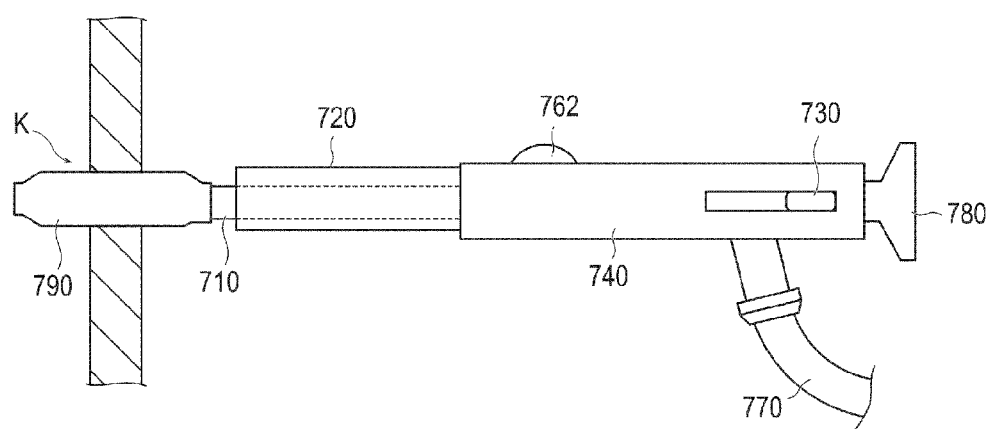
FIG. 22 is a diagram showing a state where an inflation section is disposed in a stenosed natural ostium.

First, as shown in FIG. 22, the operator slides the movement section 730 to the right side to expose the inflation section 790 from the second elongated member 720, and, in this state, gradually inserts the medical instrument 7 via the nasal cavity into the paranasal sinus to dispose the inflation section 790 in the stenosed natural ostium K. In this instance, the insertion can be achieved while changing the direction of the bend section 761 by operating the bending operating part 762.

Figure 23:
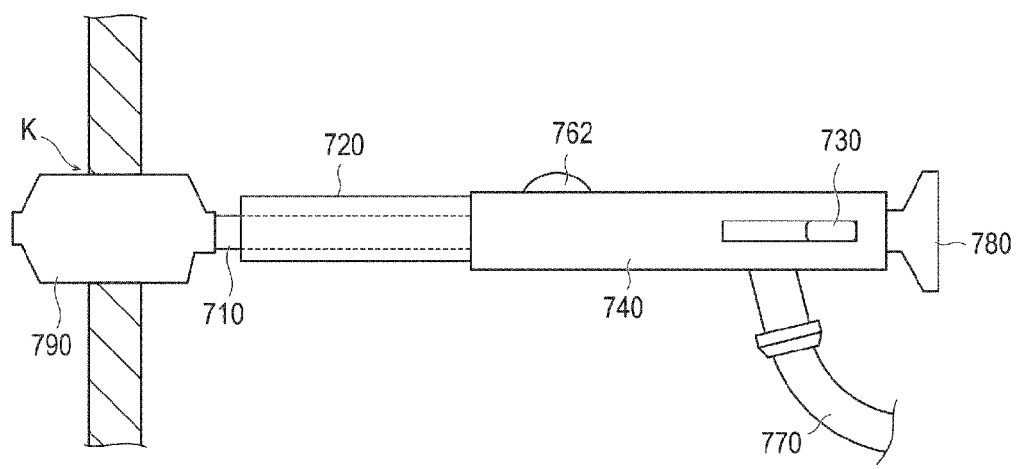
FIG. 23 is a diagram showing a state where the inflation section is inflated to dilate the natural ostium.

Next, as shown in FIG. 23, the operator inflates the inflation section 790, thereby to dilate the stenosed natural ostium K. Specifically, the inflation is effected by supplying the inflating fluid F1 via the supply section 770 into the space 790S of the inflation section 790 (refer to arrow F1 in FIG. 20).

Figure 24:
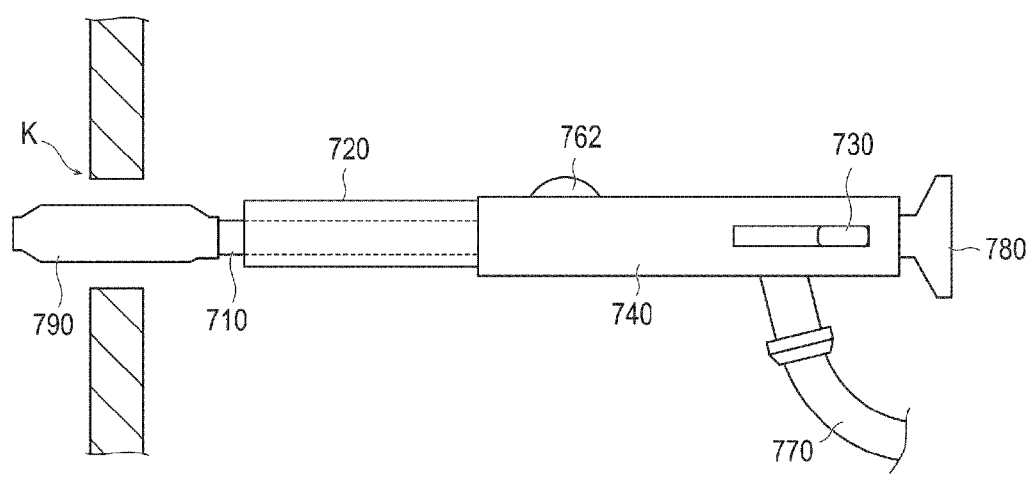
FIG. 24 is a diagram showing a state where the inflation section is deflated.

Subsequently, as shown in FIG. 24, the operator deflates the inflation section 790. Specifically, the deflation of the inflation section 790 is effected by drawing the inflating fluid F1 out of the space 790S. In this instance, the natural ostium K remains in the dilated state because it has been deformed by the inflation section 790.

Figure 25:
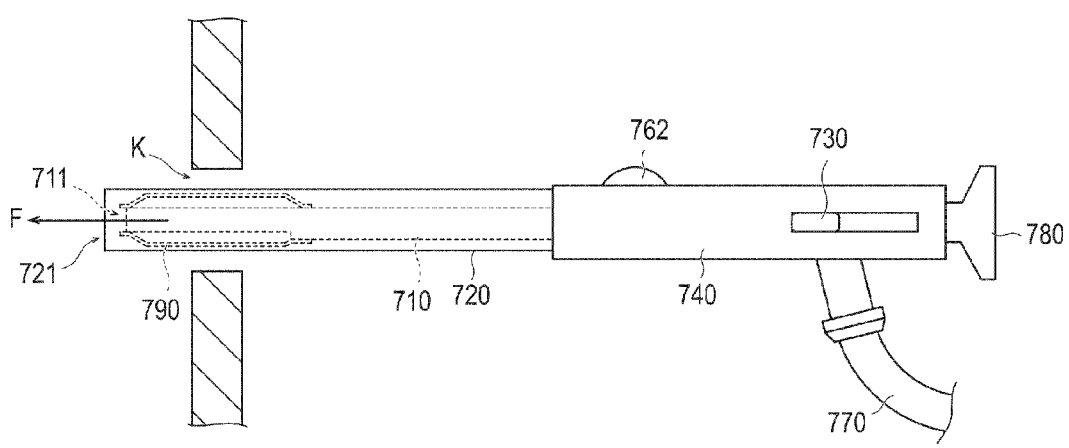
FIG. 25 is a diagram showing a manner in which a discharge section of a second elongated member is positioned on a distal side of an aperture of a first elongated member and a fluid is supplied.

Next, as shown in FIG. 25, the operator slides the movement section 730 to the left side to move the discharge section 721 of the second elongated member 720 to the distal side of the dilated natural ostium K. The fluid F is then supplied into the paranasal sinus. Specifically, the fluid F is supplied via the supply section 770 into the fluid lumen 710L, and, after passing through the aperture 711, is discharged through the discharge section 721 to be supplied into the paranasal sinus.

Modification

In the first to fourth embodiments of the present disclosure, the second elongated member 20, 220, 320 or 420 is so provided as to be able to advance and recede along the outer surface 10S, 210S, 310S or 410S of the first elongated member 10, 210, 310 or 410. However, the first elongated member 10, 210, 310 or 410 may be so provided as to be able to advance and recede along the inner surface of the second elongated member 20, 220, 320 or 420. In this case, for example in the first embodiment, the second elongated member 20 is disposed at the natural ostium K by moving the first elongated member 10 and the second elongated member 20 distally after moving the first elongated member 10 proximally in the step shown in FIG. 9.

Figure 26:
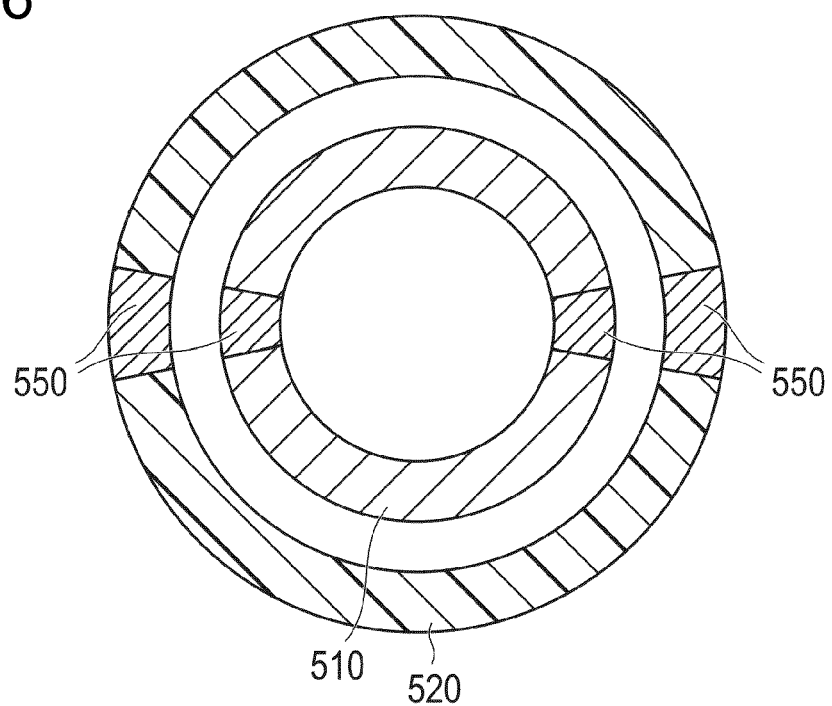
FIG. 26 is a front sectional view showing a medical instrument according to a modification example of the present disclosure.

In the first embodiment of the present disclosure, the rigidity members 50 are configured by use of wires. As shown in FIG. 26, however, rigidity members 550 may be configured by use of a material which is higher in rigidity than the other parts of a first elongated member 510 and a second elongated member 520.

Figure 27:
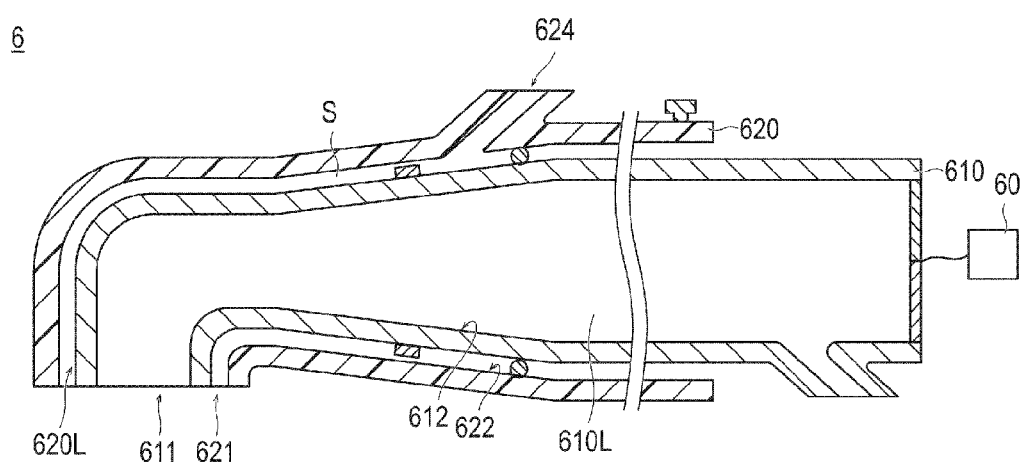
FIG. 27 is a front sectional view showing a medical instrument according to another modification example of the present disclosure.
Figure 28:
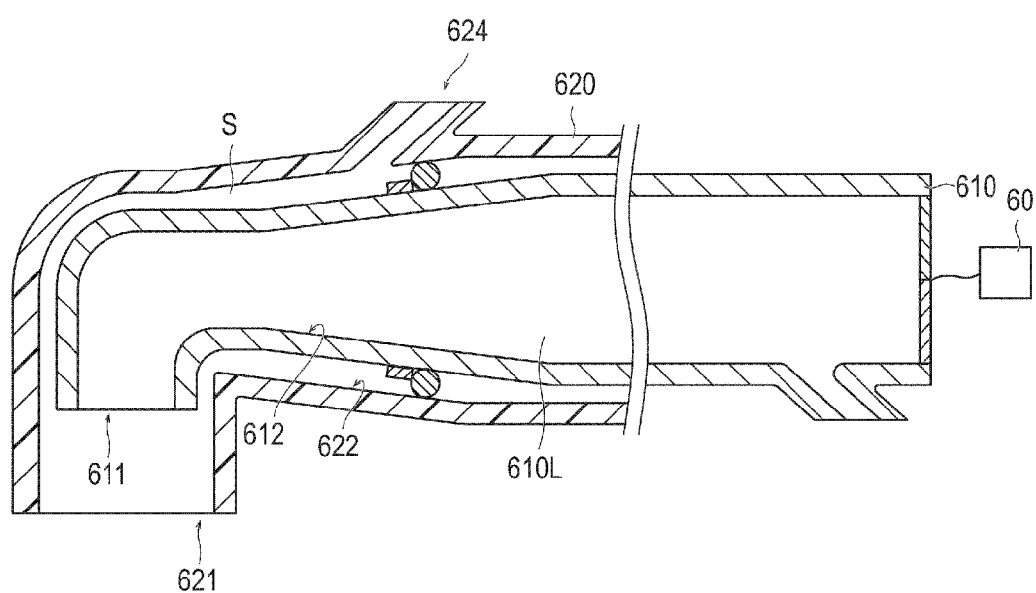
FIG. 28 is a front sectional view showing a state where a discharge section of a second elongated member is positioned on a distal side of an aperture of a first elongated member, in the medical instrument according to the modification example shown in FIG. 27.

In the first embodiment of the present disclosure, the fluid F is supplied into a living body through the supply section 14 formed on the proximal side of the first elongated member 10 and through the fluid lumen 10L. As shown in FIG. 27, however, the fluid F may be supplied into a paranasal sinus by supplying the fluid F into a gap S formed between a first elongated member 610 and a second elongated member 620 via a fluid supply section 624 formed as part of the second elongated member 620. Furthermore, a medical instrument 6 may further have a fluid suction section 60 for sucking out the fluid F through a fluid lumen 610L of the first elongated member 610. According to this configuration, it is possible not only to supply the fluid F into the paranasal sinus through the fluid supply section 624 but also to suck out mucus and/or body fluid present in the paranasal sinus by the fluid suction section 60, whereby the function of the medical instrument 6 is enhanced. A first taper section 612 and a second taper section 622 are positionally matched in the axial direction in a state where the first elongated member 610 is disposed in an insertion lumen 620L but the second elongated member 620 has not yet been moved relative to the first elongated member 610. Therefore, when a discharge section 621 of the second elongated member 620 is positioned on the distal side of an aperture 611 of the first elongated member 610 by a movement of the second elongated member 620, as shown in FIG. 28, the gap S between the first taper section 612 and the second taper section 622 is enlarged, permitting a larger quantity of the fluid F to be supplied therethrough. Note that a seal member 631 is an O-ring-like seal member and, therefore, can maintain its sealing properties through self-expansion even when the gap S is enlarged.

Figure 29:
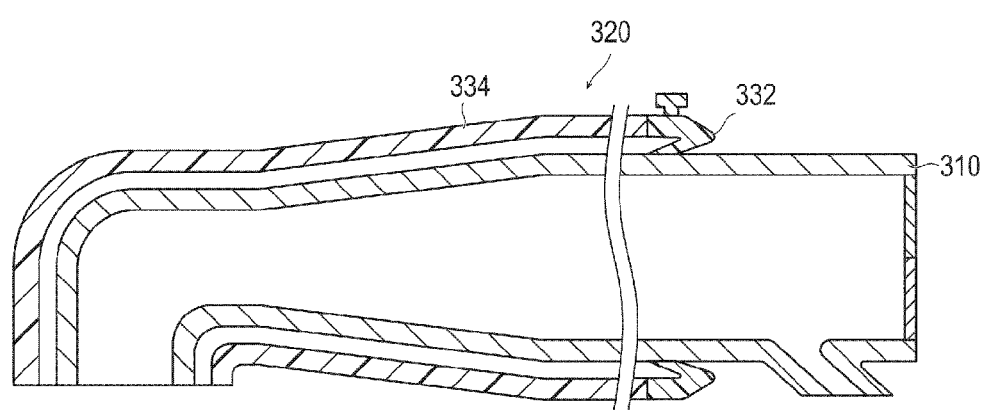
FIG. 29 is a front sectional view showing a medical instrument according to a further modification example of the present disclosure.

In the third embodiment of the present disclosure, the second elongated member 320 is configured by use of a single kind of material. As shown in FIG. 29, however, a comparatively soft material may be used for the folded-back part 332 whereas a comparatively hard material may be used for a distal-side part 334 distal of the folded-back part 332. According to this configuration, the softness of the folded-back part 332 permits the second elongated member 320 to be moved distally with a weak force, and the hardness of the distal-side part 334 distal of the folded-back part 332 ensures an enhanced insertability of the second elongated member 320 into the paranasal sinus.

In the first to fourth embodiments of the present disclosure, the operating part 32, 232, 333 or 433 constitutes the movement section 30, 230, 330 or 430 and the second elongated member 20, 220, 320 or 420 is moved distally by pushing out the operating part 32, 232, 333 or 433 distally. There may be adopted, however, a configuration in which the operating part 32, 232, 333 or 433 is not provided, and a proximal-side part of the second elongated member 20, 220, 320 or 420 is used as an operating part. According to this configuration, it is unnecessary to configure the operating part 32, 232, 333 or 433, and thus, it is possible to provide a more inexpensive and lighter-weight medical instrument.

In the first to fourth embodiments of the present disclosure, the balloon catheter 100 is inserted in the fluid lumen 10L, 210L, 310L or 410L of the first elongated member 10, 210, 310 or 410. However, a surgical knife, forceps or the like may be inserted.

In the fifth embodiment of the present disclosure, the first elongated member 710 has therein the fluid lumen 710L through which the fluid F can flow. However, a configuration may be adopted in which the first elongated member 710 does not have the fluid lumen 710L, and the fluid F flows through a gap formed around the outer periphery of the imaging section 751, inside the imaging device lumen 712L.

In the fifth embodiment of the present disclosure, the discharge section 721 of the second elongated member 720 may be positioned on the distal side of the aperture 711 of the first elongated member 710 by sliding the movement section 730 to the left side at the time of gradually inserting the medical instrument 7 into the paranasal sinus via the nasal cavity. In this instance, the medical instrument 7 may be inserted while supplying the fluid F through the supply section 770 and the discharge section 721 to the outside of the medical instrument 7, whereby it is possible to wash away foreign matter present in the insertion route ranging up to the inside of the paranasal sinus with the fluid F and to wash away dirt or contaminants, if any, present on the imaging device 750. Furthermore, the foreign matter present in the insertion route ranging up to the inside of the paranasal sinus can be drawn out through the supply section 770.

It should be understood by those skilled in the art that various modifications, combinations, sub-combinations and alterations may occur depending on design requirements and other factors insofar as they are within the scope of the appended claims or the equivalents thereof.

What is claimed is:

1. A medical instrument comprising:
a first elongated member including:
a fluid lumen through which a fluid is flowable,
a fluid supply section through which fluid is suppliable to the fluid lumen, and
an aperture opening located in a distal end surface of the first elongated member, the aperture being configured to allow fluid to exit the fluid lumen via the aperture;
a second elongated member including:
an insertion lumen in which the first elongated member is insertable, and
a discharge section through which the fluid can be discharged; and
a movement section comprising a seal member configured to form a seal between the first elongated member and the second elongated member in a state where the first elongated member is disposed in the insertion lumen of the second elongated member, the movement section being configured to allow the first elongated member and the second elongated member to move relative to each other such that the discharge section of the second elongated member is positionable on a distal side of the aperture of the first elongated member,
wherein the first elongated member is more rigid than the second elongated member, and
wherein the movement section includes an expandable and contractible bellows-like expansion-and-contraction part formed at least at a part of the second elongated member.

2. The medical instrument according to claim 1,
wherein the seal member is formed of an elastic material, and
wherein the seal member is disposed between an outer surface of the first elongated member and an inner surface of the second elongated member.

3. The medical instrument according to claim 2, further comprising a moving amount adjustment section configured to regulate a relative movement between the first elongated member and the second elongated member such that a moving amount of the movement is limited.

4. The medical instrument according to claim 2, wherein the second elongated member is configured to be advanceable and recedable along an outer surface of the first elongated member.

5. The medical instrument according to claim 1, further comprising a moving amount adjustment section configured to regulate a relative movement between the first elongated member and the second elongated member such that a moving amount of the movement is limited.

6. The medical instrument according to claim 5, wherein the second elongated member is configured to be advanceable and recedable along an outer surface of the first elongated member.

7. The medical instrument according to claim 1, wherein the second elongated member is configured to be advanceable and recedable along an outer surface of the first elongated member.

8. The medical instrument according to claim 1, further comprising:

a fluid supply section configured to permit the fluid to be supplied therethrough into a gap formed between the first elongated member and the second elongated member; and a fluid suction section configured to permit a fluid to be sucked out through the fluid lumen of the first elongated member.

9. The medical instrument according to claim 1, wherein the medical instrument is configured for use as a medical instrument for cleaning a living body organ present inside a nose of a living body.

10. The medical instrument according to claim 1, further comprising:
a main body section in which the second elongated member is disposed such that the second elongated member is slidable relative to the main body section; and
a connection section attached to the main body section, the connection section being configured to connect to an imaging device; and
an inflation section fixed to an outer periphery of the first elongated member.

11. The medical instrument according to claim 10, wherein the first elongated member further includes:
an inflating lumen through which an inflating fluid for inflating the inflation section is flowable; and
an imaging device lumen through which the imaging device is insertable and passable.

12. A medical instrument comprising:
a first elongated member including:
a fluid lumen through which a fluid is flowable,
a fluid supply section through which fluid is suppliable to the fluid lumen, and
an aperture opening located in a distal end surface of the first elongated member, the aperture being configured to allow fluid to exit the fluid lumen via the aperture;
a second elongated member including:
an insertion lumen in which the first elongated member is insertable, and
a discharge section through which the fluid can be discharged; and
a movement section comprising a seal member configured to form a seal between the first elongated member and the second elongated member in a state where the first elongated member is disposed in the insertion lumen of the second elongated member, the movement section being configured to allow the first elongated member and the second elongated member to move relative to each other such that the discharge section of the second elongated member is positionable on a distal side of the aperture of the first elongated member,
wherein the first elongated member is more rigid than the second elongated member,
wherein the first elongated member has a first tapered section in which a diameter of the fluid lumen gradually increases from a distal side toward a proximal side,
wherein the second elongated member has a second tapered section in which a diameter of the insertion lumen gradually increases from the distal side toward the proximal side, and
wherein the first tapered section and the second tapered section are configured to be disposed in an axially positionally matched state in a condition in which the first elongated member is disposed in the insertion lumen.

13. The medical instrument according to claim 12,
wherein the seal member is formed of an elastic material, and
wherein the seal member is disposed between an outer surface of the first elongated member and an inner surface of the second elongated member.

14. The medical instrument according to claim 12, further comprising a moving amount adjustment section configured to regulate a relative movement between the first elongated member and the second elongated member such that a moving amount of the movement is limited.

15. The medical instrument according to claim 12, wherein the second elongated member is configured to be advanceable and recedable along an outer surface of the first elongated member.

16. The medical instrument according to claim 12, wherein the first elongated member has a bend section formed on a distal side.

17. The medical instrument according to claim 12, further comprising:
a fluid supply section configured to permit the fluid to be supplied therethrough into a gap formed between the first elongated member and the second elongated member; and
a fluid suction section configured to permit a fluid to be sucked out through the fluid lumen of the first elongated member.

18. The medical instrument according to claim 12, wherein the medical instrument is configured for use as a medical instrument for cleaning a living body organ present inside a nose of a living body.

19. A medical instrument comprising:
a main body section;
a first elongated member including:
a fluid lumen through which a fluid is flowable,
a fluid supply section through which fluid is suppliable to the fluid lumen, and
an aperture opening located in a distal end surface of the first elongated member, the aperture being configured to allow fluid to exit the fluid lumen via the aperture;
a second elongated member disposed in the main body section such that the second elongated member is slidable relative to the main body section, the second elongated member including:
an insertion lumen in which the first elongated member is insertable, and
a discharge section through which the fluid can be discharged; and
a movement section comprising a seal member configured to form a seal between the first elongated member and the second elongated member in a state where the first elongated member is disposed in the insertion lumen of the second elongated member, the movement section being configured to allow the first elongated member and the second elongated member to move relative to each other such that the discharge section of the second elongated member is positionable on a distal side of the aperture of the first elongated member;
a connection section attached to the main body section, the connection section being configured to connect to an imaging device; and
an inflation section fixed to an outer periphery of the first elongated member,
wherein the first elongated member is more rigid than the second elongated member.

20. The medical instrument according to claim 19, wherein the first elongated member further includes:
- an inflating lumen through which an inflating fluid for inflating the inflation section is flowable; and
- an imaging device lumen through which the imaging device is insertable and passable.

\* \* \* \* \*